(12) United States Patent
Saffran

(10) Patent No.: US 9,050,393 B2
(45) Date of Patent: Jun. 9, 2015

(54) MEDICAL DEVICES AND METHODS FOR MODULATION OF PHYSIOLOGY USING DEVICE-BASED SURFACE CHEMISTRY

(76) Inventor: Bruce N. Saffran, Princeton, NJ (US)

(*) Notice: Subject to any disclaimer, the term of this patent is extended or adjusted under 35 U.S.C. 154(b) by 3188 days.

(21) Appl. No.: 11/052,204

(22) Filed: Feb. 8, 2005

(65) Prior Publication Data

US 2006/0177476 A1    Aug. 10, 2006

(51) Int. Cl.
- A61F 2/00 (2006.01)
- A61F 2/06 (2013.01)
- A61L 31/00 (2006.01)

(52) U.S. Cl.
CPC .................................. A61L 31/005 (2013.01)

(58) Field of Classification Search
None
See application file for complete search history.

(56) References Cited

U.S. PATENT DOCUMENTS

| | | | |
|---|---|---|---|
| 4,164,560 A | 8/1979 | Folkman et al. | |
| 4,389,330 A | 6/1983 | Tice et al. | |
| 4,447,590 A | 5/1984 | Szycher | |
| 4,464,317 A | 8/1984 | Thies et al. | |
| 4,530,840 A | 7/1985 | Tice et al. | |
| 4,542,025 A | 9/1985 | Tice et al. | |
| 4,591,496 A | 5/1986 | Cohen et al. | |
| 4,622,244 A | 11/1986 | Lapka et al. | |
| 4,675,189 A | 6/1987 | Kent et al. | |
| 4,698,302 A * | 10/1987 | Whitehead et al. | 435/94 |
| 4,713,243 A | 12/1987 | Schiraldi et al. | |
| 4,842,868 A | 6/1989 | Helwing | |
| 4,861,830 A | 8/1989 | Ward, Jr. | |
| 4,873,308 A | 10/1989 | Coury et al. | |
| 4,877,029 A | 10/1989 | Valentini et al. | |
| 4,879,135 A | 11/1989 | Greco et al. | |
| 4,886,062 A | 12/1989 | Wiktor | |
| 4,897,268 A | 1/1990 | Tice et al. | |
| 4,931,279 A | 6/1990 | Bawa et al. | |
| 4,941,877 A | 7/1990 | Montano, Jr. | |
| 4,943,449 A | 7/1990 | Aishima et al. | |
| 5,011,486 A | 4/1991 | Aebischer et al. | |
| 5,037,656 A | 8/1991 | Pitt et al. | |
| 5,041,100 A | 8/1991 | Rowland et al. | |
| 5,076,265 A | 12/1991 | Wokalek | |
| 5,106,627 A | 4/1992 | Aebischer et al. | |
| 5,156,843 A | 10/1992 | Leong et al. | |
| 5,156,844 A | 10/1992 | Aebischer et al. | |
| 5,166,187 A | 11/1992 | Collombel et al. | |
| 5,260,066 A | 11/1993 | Wood et al. | |
| 5,264,214 A | 11/1993 | Rhee et al. | |
| 5,282,823 A | 2/1994 | Schwartz et al. | |
| 5,290,561 A | 3/1994 | Farhadieh et al. | |
| 5,302,168 A | 4/1994 | Hess | |
| 5,324,775 A | 6/1994 | Rhee et al. | |
| 5,356,630 A | 10/1994 | Laurencin et al. | |
| 5,370,681 A | 12/1994 | Herweck et al. | |
| 5,383,928 A | 1/1995 | Scott et al. | |
| 5,405,919 A | 4/1995 | Keefer et al. | |
| 5,425,953 A | 6/1995 | Sintov et al. | |
| 5,449,382 A | 9/1995 | Dayton | |
| 5,457,093 A | 10/1995 | Cini et al. | |
| 5,464,650 A | 11/1995 | Berg et al. | |
| 5,466,262 A | 11/1995 | Saffran | |
| 5,474,563 A | 12/1995 | Myler et al. | |
| 5,512,055 A | 4/1996 | Domb et al. | |
| 5,525,357 A | 6/1996 | Keefer et al. | |
| 5,562,922 A | 10/1996 | Lambert | |
| 5,589,563 A | 12/1996 | Ward et al. | |
| 5,607,463 A | 3/1997 | Schwartz et al. | |
| 5,637,113 A | 6/1997 | Tartaglia et al. | |
| 5,650,447 A | 7/1997 | Keefer et al. | |
| 5,653,760 A | 8/1997 | Saffran | |
| 5,660,225 A | 8/1997 | Saffran | |
| 5,681,568 A | 10/1997 | Goldin et al. | |
| 5,716,981 A | 2/1998 | Hunter et al. | |
| 5,744,515 A | 4/1998 | Clapper | |
| 5,834,029 A | 11/1998 | Bellamkonda et al. | |
| 5,853,744 A | 12/1998 | Mooradian et al. | |
| 5,900,246 A | 5/1999 | Lambert | |
| 5,994,341 A | 11/1999 | Hunter et al. | |
| 6,120,536 A | 9/2000 | Ding et al. | |
| 6,146,358 A | 11/2000 | Rowe | |
| 6,174,326 B1 | 1/2001 | Kitaoka et al. | |

(Continued)

FOREIGN PATENT DOCUMENTS

| | | |
|---|---|---|
| EP | 0335341 | 10/1989 |
| EP | 0339821 | 11/1989 |

(Continued)

OTHER PUBLICATIONS

Lambert et al.; A New Method for Arterial Drug Delivery via Removable Stent; Feb. 1993.

Dev et al.; Kinetics of Drug Delivery to the Arterial Wall via Polyurethane Coated Removable Nitinol Stent-Comparative Study of 2 Drugs (abstract); 1993.

Lambert et al.; Localized Arterial Drug Delivery From a Polymer Coated Removable Metallic Stent: Kinectics and Bioactivit of Forskolin (abstract); Oct. 1993.

Eigler et al.; Local Arterial Wall Drug Delivery from a Polymer Coated Removable Metallic Stent: Kinetics, Distribution and Bioactivity of Forskolin (abstract); Feb. 1994.

Dev et al.; Kinetics of Drug Delivery to the Arterial Wall via Polyurethane Coated Removable Nitinol Stent-Comparative Study of 2 Drugs; 1995.

(Continued)

Primary Examiner — Shanon A Foley
(74) Attorney, Agent, or Firm — Dickstein Shapiro LLP

(57) ABSTRACT

This invention provides implantable medical devices having at least one moiety attached to the surface capable of catalyzing a reaction in vivo. The implantable medical device has a body such as a stent with a surface adapted to be placed adjacent to a biological tissue or fluid. The body has at least one moiety attached to the surface which is capable of catalyzing a first reaction upon contacting a first substrate in the biological tissue or fluid. The moiety remains attached to the surface after the first reaction and is capable of catalyzing at least a second reaction upon contacting a second substrate. In preferred embodiments the moiety is capable of catalyzing a multitude of reactions as substrates come into contact and then leave the surface of the device.

53 Claims, 28 Drawing Sheets

(56) References Cited

U.S. PATENT DOCUMENTS

| | | | |
|---|---|---|---|
| 6,193,746 B1 | 2/2001 | Strecker | |
| 6,273,913 B1 | 8/2001 | Wright et al. | |
| 6,436,135 B1 | 8/2002 | Goldfarb | |
| 6,545,097 B2 | 4/2003 | Pinchuk et al. | |
| 6,599,559 B1 | 7/2003 | McGee et al. | |
| 6,645,518 B2 | 11/2003 | Tedeschi et al. | |
| 6,663,863 B2 | 12/2003 | Horvath et al. | |
| 6,855,770 B2 | 2/2005 | Pinchuk et al. | |
| 7,004,976 B2 * | 2/2006 | Ornberg et al. | 623/23.58 |
| 2002/0115081 A1 * | 8/2002 | Lee et al. | 435/6 |
| 2004/0210289 A1 * | 10/2004 | Wang et al. | 607/116 |

FOREIGN PATENT DOCUMENTS

| | | |
|---|---|---|
| EP | 0449592 | 11/1994 |
| WO | WO 91/12779 | 9/1991 |
| WO | WO 93/11120 | 6/1993 |
| WO | WO-94/21308 A1 | 9/1994 |
| WO | WO 95/03036 | 2/1995 |

OTHER PUBLICATIONS

Dev et al.; Current Status and Prospects for the Use of Temporary Stents; Jul. 1994.

Litvack et al.; Current Status and Potential Applications of the Harts Removable Stent; 1994.

Eigler et al.; Implantation and Recovery of Temporary Metallic Stents in Canine Coronary Arteries; Oct. 1993.

File History for U.S. Appl. No. 08/513,092—Saffron (U.S. 5,653,760).

File History for U.S. Appl. No. 08/114,745—Saffron (U.S. 5,466,262).

File History for U.S. Appl. No. 08/557,432—Saffron (U.S. 5,660,225).

File History for U.S. Appl. No. 08/385,373—Lambert (U.S. 5,562,922).

File History for U.S. Appl. No. 08/033,394—Lambert.

File History for U.S. Appl. No. 08/094,536—Hunter.

File History for U.S. Appl. No. 08/478,203—Hunter (U.S. 5,716,981).

File History for U.S. Appl. No. 08/417,160—Hunter.

File History for U.S. Appl. No. 08/663,518—Ding (U.S. 6,120,536).

File History for U.S. Appl. No. 08/526,273—Ding.

File History for U.S. Appl. No. 08/424,884—Helmus.

File History for U.S. Appl. No. 07/853,682—Schwartz (U.S. 5,282,823).

File History for U.S. Appl. No. 08/109,149—Scott (U.S. 5,383,928).

File History for U.S. Appl. No. 07/896,240—Scott.

File History for U.S. Appl. No. 081355,402—Tartaglia (U.S. 5,637,113).

File History for U.S. Appl. No. 08/707,820—Strecker—(U.S. 6,193,746).

File History for U.S. Appl. No. 08/393,950—Strecker.

File History for U.S. Appl. No. 08/087,520—Strecker.

File History for U.S. Appl. No. 08/280,646—Bellamkonda (U.S. 5,834,029).

File History for U.S. Appl. No. 07/273,236—Aebischer (U.S. 5,011,486).

Textbook of Polymer Science, 3rd Ed., John Wile & Sons 1984—F. W. Billmeyer.

Intemolecular and Surface Forces, 2nd Ed., Academic Press (1992)—Jacob N. Israealachvili.

Hydrophobic Interactions, Plenum Press (1980)—Arieh Ben-Naim.

Cardosi, M.F. "Covalent Immobilization of Enzymes to Graphitic Particles. Immobilization of Enzymes and Cells" (1997), (ed. G. Bickerstaff), Humana Press, pp. 217-227.

Davis, J. et al., "Preparation and Characterization of a novel redox polymer based on salicyl-N-phenylene-1,4,-diamine," J. of Electroanalytical Chem., 403, 1996, pp. 213-218.

Greene, Theodora W. et al., "Protective Groups in Organic Synthesis", 3rd Edition, Jun. 1999 ISBN: 0-471-16019-9—John Wiley & Sons, Inc.

Johnston, D. A. et al., "The Electrochemistry of Hydrogen Peroxide on Evaporated Gold/Palladium Composite Electrodes. Manufacture and Electrochemical Characterization," Electroanalysis, 7, No. 6, 1995, pp. 520-526.

Kluger, Ronald et al., "Activation of Acyl Phosphate Monoesters by Lanthanide Ions: Enhanced Reactivity of Benzoyl Methyl Phosphate," *J. Am. Chem. Soc.* 2002, 124, pp. 3303-3308.

Kluger, Ronald et al., "Biomimetically Activated Amino Acids. Catalysis in Hydrolysis of Alanyl Ethyl Phosphate," J. Am. Chem. Soc. 1997, 119, pp. 12089-12094.

Kumita, J. et al., "Photo-control of helix content in a short peptide," Proc. Nat'l Acad. Sci. USA, vol. 97, No. 8, Apr. 11, 2000, pp. 3803-3808.

Molloy, C., "Signal Transduction Targets Involved in Fibroproliferative Vascular Diseases," Current Pharmaceutical Design, 1997, 3, pp. 585-596.

Schneider, R. et al., "A novel modular mosaic of cell adhesion motifs in the extracellular domains of the neurogenic *trk* and *trkB* tyrosine kinase receptors," Oncogene, 6, 1991, pp. 1807-1811.

Shallenberger, J.R. et al., "Adsorption of polyamides and polyamide-silane mixtures at glass surfaces," Surface and Interface Analysis, 35, 2003, pp. 667-672.

Velentza, A. et al., "A Protein Kinase Associated with Apoptosis and Tumor Suppression," J. of Biol. Chem., vol. 276, No. 42, Oct. 19, 2001, pp. 38956-38965.

Wiesmann, C. et al., "Nerve growth factor: structure and function," Cell. Mol. Life Sci. 58, 2001 pp. 748-759.

Willner and Willner, "Molecular and biomolecular optoelectronics," Pure Appl. Chem, vol. 73, No. 3, 2001, pp. 535-542.

Zhang J. et al., "PATIC: a conformationally constrained photoisomerizable amino acid," J. Peptide Res., 1999, 53, pp. 560-568.

Decisions in Tennessee Eastman v. Commissioner of Patents and Imperial Chemical Industries Ltd. v. Commissioner of Patents, 1974.

*New methods of drug delivery*, Robert Langer, American Assoc. for the Advancement of Science, Sep. 28, 1990, pp. 1527-1533.

*Present and future applications of biomaterials in controlled drug delivery systems*, R.S. Langer, N.A. Peppas, Biomaterials 1981, vol. 2 October, pp. 201-214.

*Localized Arterial Wall Drug Delivery From a Polymer-Coated Removably Metallic Stent*, Thomas Lambert, et al., Circulation vol. 90, No. 2, Aug. 1994, pp. 1003-1011.

*Regeneration of Transected Sciatic Nerves Through Semi-Permeable Nerve Guidance Channels*, Aebischer et al., American Society for Artificial Internal Organs, pp. 474-477, 1986.

*The Role of Cytoplasmic Microtubules in Regulation of Smooth Muscle Proliferation*, Katsuda et al., 8th International Symposium on Atherosclerosis, Oct. 9-13, 1988, p. 446.

*The use of a semi-permeable tube as a guidance channel for a transected rabbit optic nerve*, Aebischer et al., Brain Research, vol. 78, pp. 599-603, 1988.

*Basic Fibroblast Growth Factor Released From Synthetic Guidance Channels Facilities Peripheral Nerve Regeneration Across Long Nerve Gaps*, Aebischer et al., Journal of Neuroscience Research, 1989, pp. 282-289.

*The Role of Cytoplasmic Microtubules in Regulation of Smooth Muscle Proliferation*, Katsuda et al., Clinica & Terapia Cardiovascolare, 1990, pp. 245-248.

* cited by examiner

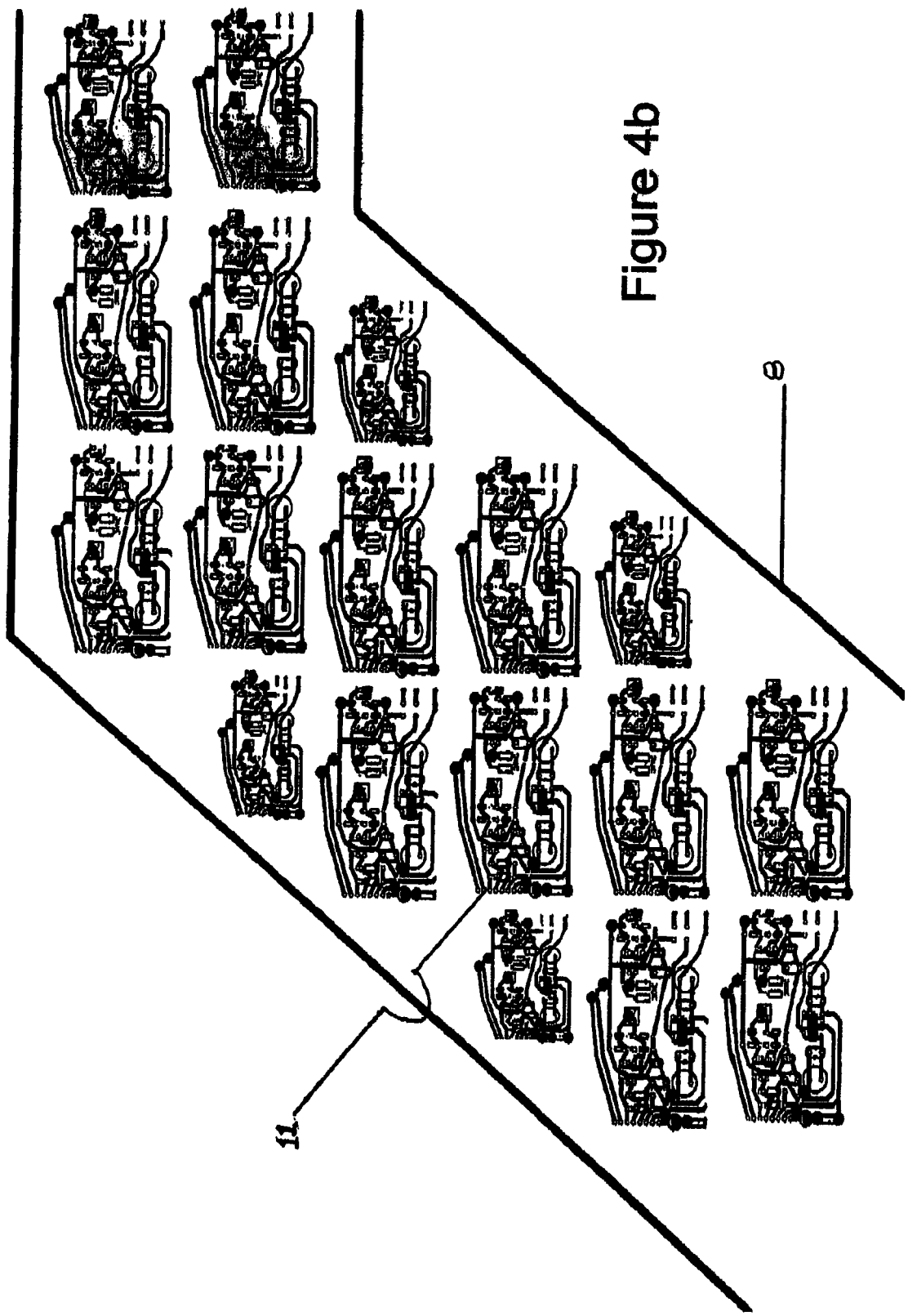

SEQUENCE LISTING

```
<160> NUMBER OF SEQ ID NOS: 4

<210> SEQ ID NO 1
<211> LENGTH: 53
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
```

```
gggggggtc tcagcgctct tgatccaggg atgctgcaa                          39
```

```
<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggggggtc tcagcgctac taagtgcctg ttgtgtatc                         39

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Pro Lys Asp Thr Gln Gln Ala Leu Ser Arg Lys
 1               5                  10
```

MEDICAL DEVICES AND METHODS FOR MODULATION OF PHYSIOLOGY USING DEVICE-BASED SURFACE CHEMISTRY

FIELD OF THE INVENTION

This invention relates to the treatment of tissues in human or veterinary medicine. Medical devices and methods according to preferred embodiments of the invention are capable of both a mechanical stabilization function and of facilitating chemical reactions at the site of tissue injury to improve healing or promote other biological functions.

In contrast to current "drug-eluting" medical devices, apparatus and methods of this invention need not elute a treating material. The chemical moieties of the present invention may be covalently attached to a surface of a device according to the invention and are capable of facilitating membrane-based physiological processes without washing away or being internalized. These chemical moieties can be attached to the surface of a device either during initial manufacture or after modification in situ. Since devices according to certain embodiments of this invention also can be modified after deployment in vivo, they allow for initiation or cessation of catalyzed biological processes which are different from those which were present at the time of initial deployment or implantation.

Devices and methods of this invention can be used for treatment of vascular injuries, and many other conditions, including, but not limited to, infections, metabolic conditions such as osteoporosis, hypertension, and diabetes, neoplastic disease, and traumatic injuries. They can be further utilized to treat biological fluids in vitro, or modify cellular physiology in tissue culture.

BACKGROUND OF THE INVENTION

Previous drug eluting devices, such as, for example, vascular stents have generally failed to restrain hydrophilic medicines at the site of injury or damaged tissue. Although the use of the present invention is not limited to deployment at the sites of vascular injury, the problems encountered in that model serve to frame this invention and how it provides a new approach to previously encountered roadblocks in the local treatment of injury or disease.

Drug eluting stent (DES) technology has been known in the art for approximately ten years. Ten years ago, a major problem faced by angiographers was that once a stent was deployed in a vessel, especially in an end-vessel system such as the coronary system, there was a high incidence of vascular thrombosis in the newly deployed stent lumen. At the time, investigators focused their efforts on preventing acute thrombosis by delivering Heparin, a potent hydrophilic parenteral anticoagulant, from the stent surface (U.S. Pat. No. 5,383, 928). Restenosis, the process of late lumen loss due to neointimal hypertrophy, was also investigated by the elution of both hydrophobic and hydrophilic molecules to attempt to slow or prevent this process (U.S. Pat. No. 5,464,650), but these, too, efforts were largely unsuccessful. The problem was either that the treatment compounds were not sufficiently restrained by the stent or were rapidly solubilized in the aqueous environment of blood and quickly washed away from the site of injury.

Recently, Tedeschi et al (U.S. Pat. No. 6,645,518) refer to the use of a specialized coating which is capable of binding and releasing hydrophobic medicines in solution. They also refer to incorporation of hydrophilic medicines in a polymeric compound composed of a polyisocyanate; an amine donor and/or a hydroxyl donor; an isocyanatosilane adduct having terminal isocyanate groups and at least one hydrolysable alkoxy group bonded to silicon; together with a polymer base. This mixture swells when hydrated and can as such be loaded with medicine dispersed in the hydrating solution. After deployment in aqueous solution, the medicine is then released. However, they describe no means to restrain the medicine after release such that it remains available to damaged tissues locally. Once released, the hydrophilic medicine is free to drift away in solution from the treatment site away from where it is needed.

Also described in the work of Tedeschi et al. (U.S. Pat. No. 6,645,518) is how covalent bonds can be used to regulate drug release: "In a most preferred embodiment, the nucleophilic nitrogen atoms of the polyurea network are allowed to react with an organic or inorganic compound to form a covalent bond. The resulting coating-active agent bond preferably cleaves to release the active agent when used on a medical device in an environment which can cleave the bond." Once released, however, the treating material is free to float away.

Several other investigators have discussed the covalent linking of a macromolecule to the surface of a device to alter the local treating environment. For example, Ward and others (U.S. Pat. Nos. 4,861,830, 5,589,563) refer to methods of treating the surface of a device to improve flow dynamics of blood along the surface of a device by changing the hydrophobicity of polymers attached to the surface. These properties have also been referred to by McGee and colleagues (U.S. Pat. No. 6,599,559). Schwartz, et al. (U.S. Pat. No. 5,607,463) refers to how adding atoms of group 5b of the periodic table can be used to improve the binding properties of a polymer to a metal device surface. In contrast, Saffran has disclosed the use of elutable molecules and molecules bound by a hydrolysable bond to alter the biology of neighboring cells in vivo through a method of "directional presentation" of a treating material (U.S. Pat. Nos. 5,660,225, 5,466,262 and 5,653,760).

Clapper (U.S. Pat. No. 5,744,515) refers to the promotion of graft endothelialization by directional presentation of cell adhesion molecules on the device surface. The affixed molecules in Clapper are said to have an adhesive function. Horvath et al. (U.S. Pat. No. 6,663,863) refer to the use of medicines derived from the complement cluster domains of the immune system to inhibit cell adhesion. Injection of such compounds at the time of stenting is said to inhibit recruitment and/or adhesion of cells to the stent. No means for limiting the systemic response of these drugs to only those cells in the vicinity of the stent is disclosed.

What is needed, however, is a means to both deliver and restrain medicinal functional groups primarily at the site of injury without their floating away in the blood stream and without their being "used up" after contact with the first cell to utilize them.

One embodiment of the present invention provides apparatus and methods of tissue stabilization and/or treatment by which the functional elements of treating materials are retained at the site of injury.

Another embodiment of the present invention provides methods and apparatus that serve as a surface for catalysis of cell membrane reactions, thereby providing a substantially undepletable source of treating material to tissues adjacent to the device.

Another embodiment of the present invention provides methods and apparatus for treatment of fluids within the body by providing on the surface of the device the active sites of specific plasma-borne enzymes, hormones or growth factors, thereby permitting device-directed catalysis of specific humeral reactions.

A further embodiment of the present invention provides methods and apparatus for surface catalysis, the chemical properties of which can be modified after the device has been deployed.

A further embodiment of this invention provides methods and apparatus for surface catalysis that can present a multitude of differing molecular moieties simultaneously.

A further embodiment of the present invention provides reactive surfaces and methods capable of converting pro-drugs to biologically active drugs at the site of device deployment.

Additional embodiments of the present invention provide methods and devices for surface catalysis that can be deployed via endoscope, catheter, needle, or open surgical procedure that can provide structural support to hollow viscera, solid organs, or blood vessels.

Other embodiments and advantages of the invention will be apparent from the following summary and detailed description together with the accompanying Figures.

BRIEF SUMMARY OF THE INVENTION

This invention provides implantable medical devices having at least one moiety attached to the surface and related methods of catalyzing a physiological reaction in vivo. In accordance with preferred embodiments of the invention, a moiety remaining attached to the surface of the implantable device can catalyze multiple physiological reactions.

One embodiment of the invention provides an implantable medical device having a body with a surface adapted to be placed adjacent to a biological tissue or fluid. The body has at least one moiety attached to the surface which is capable of catalyzing a first reaction upon contacting a first substrate in the biological tissue or fluid. The moiety remains attached to the surface after the first reaction and is capable of catalyzing at least a second reaction upon contacting a second substrate. In preferred embodiments the moiety is capable of catalyzing a multitude of reactions as substrates come into contact and then leave the surface of the device.

In another embodiment of the invention, a second moiety is attached to the surface. Each moiety can catalyze a different reaction upon contacting one or more substrates in vivo.

The moieties can be attached to the surface by a variety of bonds (e.g., non-hydrolyzable, covalent, and metaloxysi-lane). The moieties can include, but are not limited to, proteins, aptamers, FMN, diopterins, redox compounds, enzymes, growth factors, hormones, nucleic acids, ribozymes, and siRNA. In another embodiment, the moiety may be structurally modified in situ by application of energy to the device.

The body may comprise a variety of materials including, but not limited to polymeric material and metallic material. In one embodiment, the body is flexible (e.g., a flexible sheet or layer such as a metallic stent).

Also provided herein are methods of catalyzing a physiological reaction in vivo. In one embodiment, the method comprises providing an implantable device having a body and a surface on the body adapted for placement adjacent to a biological tissue or fluid in vivo. At least one chemical moiety is attached to the surface. The moiety attached to the surface is capable of catalyzing a first reaction upon contacting a first substrate in the biological tissue or fluid and remaining attached to the surface after the first reaction for catalyzing a second reaction upon contact with a second substrate.

Additional embodiments of the present invention will be set forth in part in the description that follows, and in part will be obvious from the description, or may be learned through the practice of the invention.

BRIEF DESCRIPTION OF THE DRAWINGS

FIG. 4b shows a lower power view of the exemplary arrangement of FIG. 4a placed on a vascular stent.

FIG. 6a shows the device rendered "protected" by coating (30), whereas FIG. 6b depicts the dissolution of the coating (32) by a solvent (31) according to preferred embodiments of the invention.

FIGS. 7a and 7b depict a transistor. When energy is applied to the device, current will flow as depicted in 7b. This concept is applied to the manufacture of a device according to this embodiment of this invention as layered semiconductors with the appropriate doping pattern, e.g., PNP. An array of moieties such as enzymes on the surface of a device according to this embodiment of the invention is depicted in FIGS. 7c and 7d. FIG. 7c shows the enzymes in cis configuration (28), e.g., inactive, following an energy pulse and 7d shows the switching "on" of the affixed enzymes resulting from a change of electron flow through the device.

FIGS. 8 a-b are amino acid diagrams depicting an embodiment of the invention having an EGF moiety (SEQ ID NO: 1). The activity of the EGF moiety is controlled by a photoisomer, in this case Azobenzine.

FIG. 9a shows the device being used to treat fluids in vitro in series with flowing blood, e.g., during hemodialysis. FIG. 9b shows one embodiment of the invention being used to treat intravenous fluids. FIG. 9c depicts the device being used to regulate cell growth and function in vitro.

FIGURE LABELS

Figure 1A:
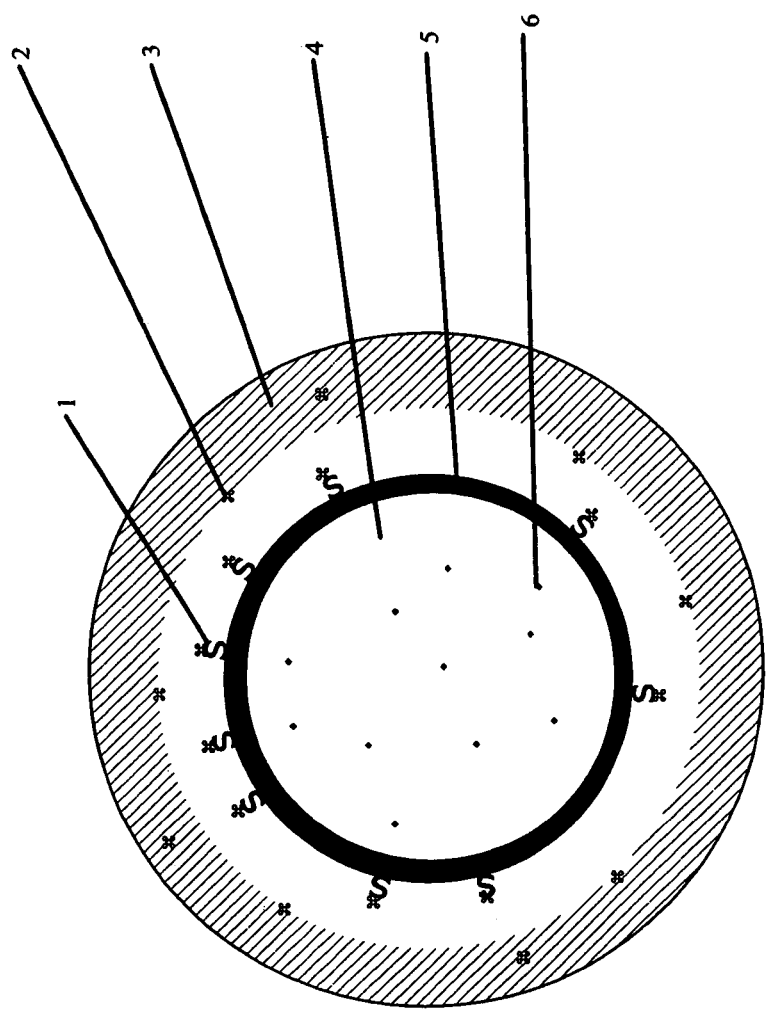
FIG. 1a illustrates bonding of a treating material to an implantable device, lysis of the bond, and subsequent transit of the drug from the device surface to the tissue in accordance with the prior art.

1) Non-Covalent Linkage of Treating Material to Device
2) Treating Material Having Been Released From Device
3) Tissue Being Treated
4) Lumen of Blood Vessel
5) Vascular Stent Metal
6) Endoluminal Contents
7) Primary R-Group available for addition of chemical group
8) Surface of body onto which active moiety has been covalently bound
9) Active moiety, e.g., active site of an enzyme, which has biological activity
10) Silane covalent linkage of active moiety to surface
11) One embodiment of a printed-circuit arrangement of treating materials on surface of a stent
12) Secondary R-Group available for addition of chemical group
13) Linker bond of carboxy terminus of illustrative active moiety to the covalently bound silane.
14) Substrate on tissue being treated
15) Dimerized EGF at the EGF receptor
16) Non-Dimerized portion of EGF molecule
17) Extracellular portion of EGF receptor
18) Intramembrane portion of EGF receptor
19) Hydrophilic component of plasma membrane
20) Hydrophobic component of plasma membrane
21) Intracellular (kinase-linked) portion of EGF receptor
22) Target of kinase prior to phosphorylation
23) Target of kinase after phosphorylation
24) A first type of treating moiety
25) A second type of treating moiety
26) A third type of treating moiety
27) Pattern of biologically-active moieties on surface of a vascular stent
28) A cis type carbon-carbon bond
29) A trans type carbon-carbon bond
30) Protective coating prior to exposure of enzymatic moieties
31) Solvent capable of dissolving protective coating
32) Fragment of coating
33) Source of a transistor
34) Drain of transistor
35) Gate of transistor
36) Additional binding site on enzyme moiety similar in function to "9" but different location on the protein
37) Cells growing on device
38) Biological material on cellular side of the device
39) Biological material on side of device opposite to cells
40) Arrows indicating fluid flow
41) EGF bound by silane linkage
42) Dimerized EGF
43) EGF binding moiety of the EGF receptor
44) Intracellular kinase-activating portion of the EGF receptor
45) Pro-drug
46) Active drug
47) Inflow to device
48) Effluent from device
49) Arrow demonstrating direction of flow
50) Arrow indicating reaction on surface of device converting pro-drug to active drug
51) Active site of the protein capable of binding the receptor
52) Cystene-linkage (14-31) of the protein
53) Azobenzine in trans configuration
54) Azobenzine in cis configuration
55) Arrow showing flow of electric current
56) Widened "active site", rendered inactive by Azobenzine-induced misfolding

DETAILED DESCRIPTION OF THE INVENTION

Preferred embodiments of the invention provide implantable devices having a body with a surface with chemical moieties which can be used to carry out a variety of functions (e.g., catalyze reactions, convert prodrugs to active drugs, and bind to cell surface receptors). The chemical moieties can remain bound to the surface of the device permitting the implantable devices to carry out their function multiple times. The preferred implantable devices of the invention therefore do not require elution of a treating material. The treating component of preferred embodiments of the invention is a chemical at the device surface such that the surface itself is capable of catalyzing a particular reaction or reactions, depending on the local chemistry of the surface molecules on the device. Thus, the biological activity of the device can result from a modification of the device surface itself, rather than from a molecule embedded for release. The target tissue or biological fluid need only come in contact with the active moiety on the device surface to be treated. Preferred embodiments of the invention are directed to reactions regulated by the activation of cell membrane bound receptors which come in contact with the moieties bound to the surface of the devices. Various moieties (e.g., fluid-borne molecules, heme and flavin diopterins (e.g., FAD, FMN, and NADP), protein-bound macromolecules, nucleic acids, enzymes, proteins, and hormones) can be modified via the catalytic properties of devices according to embodiments of this invention.

A suitable analogy for one embodiment of this invention involves the welding of padlock keys onto a metal bar. One would subsequently bring a series of locked padlocks over to the keys mounted on the bar and attempt to open them. Some locks would fit the keys, and others would not. The locks which open must either stay on the correct key, or leave the bar without the key (the key remains welded to the bar). Each key is never used up, as it remains welded to the bar and cannot dissociate with the lock. Furthermore, each key can open many locks, as long as the lock to be opened has the correct configuration.

The lock and key analogy is representative of one mechanism of enzymatic specificity. Embodiments of this invention providing covalent linkages of enzyme macromolecules to a device, placed in such a way as to expose the active site of the enzyme, can be used to catalyze specific reactions on a cell surface without significant depletion of the active moiety by receptor mediated endocytosis. Once a receptor-ligand interaction occurs, the intracellular cascade is set into motion. The cell either may stay on the device surface, or move along.

As discussed above, previous attempts at preventing vascular restenosis using stents that eluted hydrophilic drugs, e.g., heparin, were largely unsuccessful. Despite delivery to the injured vessel wall, the hydrophilic compounds were not restrained by the device sufficiently at the site of injury to be efficacious. Because thermodynamic forces force hydrophilic drugs into aqueous solution, hydrophilic molecules cannot be restrained on the stent using the previous DES paradigm.

The present invention overcomes this problem by binding molecules, for example, either an entire hydrophilic molecule, or a portion of it, covalently to the device or stent itself. By doing so, the active site of the molecule or drug, i.e., that which binds to the cell membrane receptor and activates it, can be exposed such that it can bind to its partner molecule on the cell surface, not unlike the keys on a bar analogy provided above. As such, the device according to an embodiment of the present invention has bound to its surface molecules which can mimic the structure of naturally-occurring hydrophilic ligands upon which cell membrane-based surface receptors can bind and are thereby activated. Furthermore, the device can also catalyze reactions which convert pro-drugs to active drugs on the surface of the device. This provides specificity in the site of action of such drugs because the pro-drugs can be administered systemically or enterically, and converted to their active forms by the device of the invention at only or preferentially at the sites where they are needed.

One of the hallmarks of biologically-active molecules, particularly hydrophilic molecules or functional groups, is that they carry an electric charge. Water is a polar molecule and as such is an excellent solvent for those compounds expressing an ionic arrangement on their surface. As a charged moiety, a hydrophilic group can be influenced by local electrostatic and magnetic fields more than would be a hydrophobic compound. The electromagnetic properties of functional groups provide, according to another embodiment of the present invention, a method of controllability—their physical conformation, and thereby their biological activity, can be altered by altering their local electromagnetic field.

According to preferred embodiments of the invention, devices can be manufactured, for example, from a thin metal sheet such as a metal stent. Once the device is deployed, the exposed active sites and the bonds affixing them to the metal conform to the most thermodynamically stable arrangement in blood plasma, i.e., the arrangement with the lowest delta G given the prevailing local electromagnetic and physiochemical forces. If, however, energy is added to the system, these forces strive for a new equilibrium given the new energy balance. For example, if the bonds originally holding a particular moiety to the metal were in cis configuration, they could covert to trans which is, overall, more thermodynamically favorable, if given a pulse of externally applied energy with the correct wavelength as a mechanism of molecular switching to control the biological activity of the medical device.

In accordance with this invention externally applied energy can alter the local electromagnetic forces of the implantable device. Depending on the bond used to link the hydrophilic group to the device, or the particular chemistry of the particular active site, the energy needed to transform the bonds and thus configuration of the device-based ligand will be different. The amount of energy is readily ascertainable by one of ordinary skill in the art given the teachings here. The "turning off" and "turning on" of the activity of an attached group is accomplished by providing the appropriate external energy bolus to the device. Bolus duration and frequency for a particular enzyme, hormone, or growth factor moiety can readily be determined given the teachings herein and using enzymatic activity tools or ELISA.

In another embodiment optimal enzymatic configurations can be replicated over an area of metal or other suitable reactive surface, as is done in printed circuit technology. In a more complex embodiment of this invention, a metal stent or the like can be manufactured as a microchip, complete with a tiny photocell. After binding an enzymatic array in the desired manner, the activities of the moieties can be controlled by stimulation of the photocell. The activity of the enzymes, hormones or growth factor moieties on the surface of the device can also be controlled by a circuit in the device—much like the liquid crystal display on the surface of the common calculator is controlled by the microchip embedded in the housing.

Figure 1B:
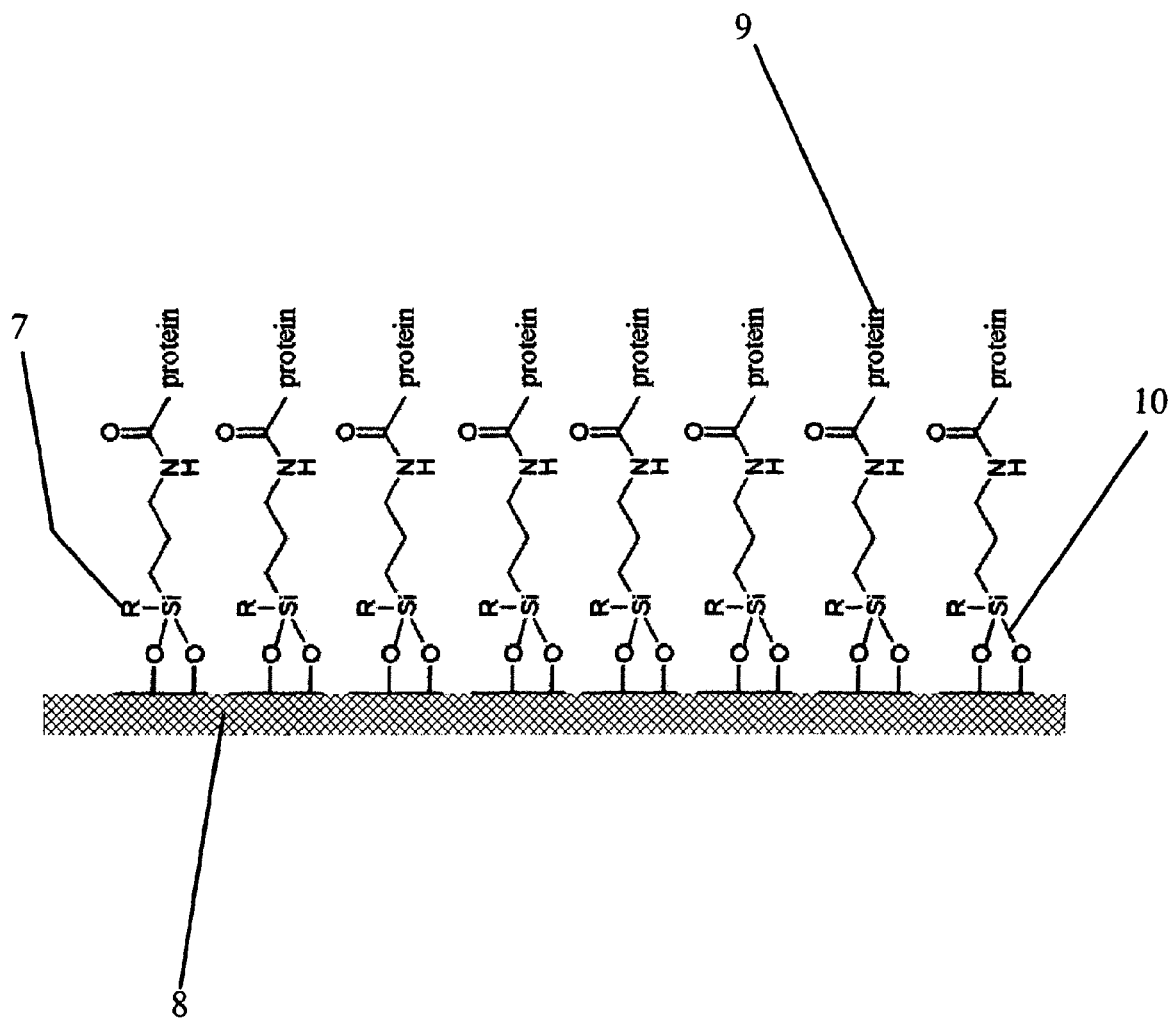
FIG. 1b depicts a non-hydrolysable bond (10) linking the active site of moiety (9), e.g., a protein, to the surface of a device (8) according to a preferred embodiment of the invention.

Referring now to the Figures, FIG. 1a is taken from aspects of the prior art. FIG. 1b is a depiction of aspects of the present invention. In the former, the treating material (2) is linked to the device (5) with a hydrolysable bond (1) or contained in interstices of the surface and is subsequently released into solution (6). The treating material then is substantially retained within the target tissue (3). The lumen of the vessel (4) and plasma elements (6) are shown for orientation. In contrast, in accordance with an embodiment of the present invention shown in FIG. 1b, the active site of a treating material (9) is covalently linked via a non hydrolysable linkage, e.g., a silane bond (10), and is not released from the surface of the device (8).

Previously, drugs associated with devices served not as a catalyst, but as detachable entities (2) which ultimately disengage from the device (5) and become incorporated in a cell (3). Such drugs are first presented to the injured tissue and then, after presentation, detach from the device, or first elute prior to cellular uptake following lysis of a linker bond. The process of linking a drug to the device in this fashion has been known in the art and recently reviewed by Mooradian, et al. (U.S. Pat. No. 5,853,744). Each drug molecule (2) is typically used only once, either by becoming incorporated in the tissue or rendered inaccessible to other cells by an overlying cell.

Figure 1C:
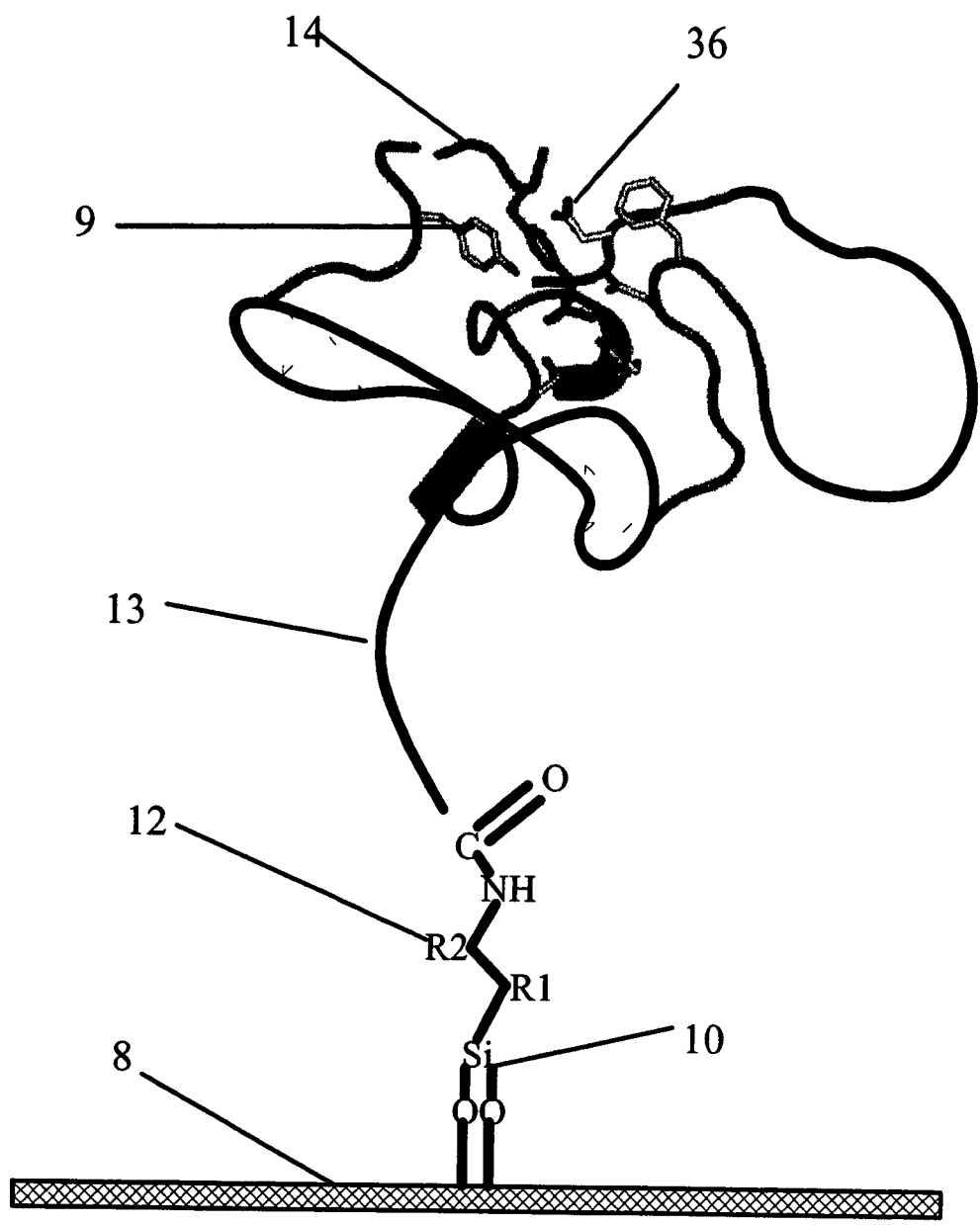
FIG. 1c shows the reactive surface of an implantable device with a tyrosine phosphate 1B enzyme (PTP1B) moiety (9) linked by silane linkage (10) to the supporting surface of a device (8) in accordance with one embodiment of the invention.

In contrast, the present invention (e.g., FIG. 1b) presents the active sites of treating materials (9), typically enzymes, nucleic acids, aptamers, hormones or growth factors bound covalently upon the surface of the device (8) with a substantially non-hydrolizable linkage, e.g., a silane bond (10). Exemplary reactions forming silane bonds are shown below and in the art (see, e.g., Davis, J., Vaughan, D. H. & Cardosi, M. F., Preparation and Characterization of a novel redox polymer based on Salicyl-N-Phenylene-1,4,-Diamine, J. Electroanal. Chem., 403, 213-218 (1996) and Cardosi, M. F., Enzyme immobilisation on graphitic carbon particles. Immobilisation of Enzymes and Cells. (1997), (ed. G. Bickerstaff), Humana Press, pp. 217-228). As shown in FIG. 1c, an enzyme is linked via a non-hydrolysable bond (10) to an inactive portion of the enzyme (13) and then to the (8). The covalently attached treating materials can serve to catalyze reactions on the surface of cells or upon substrates contained within fluid in contact with the device.

The inactive portion of the enzyme protein (13) may be affixed to the surface of the device (8) by a silane linkage (10) as depicted in FIG. 1c. The "R" sites (12) can contain molecules with specific ionic properties, which can subsequently be used to modify the presentation angle of the active site to the surrounding biological environment. Affixation of these "R" groups to the linker bond and their modification in vivo are discussed in detail below.

Figure 1D:
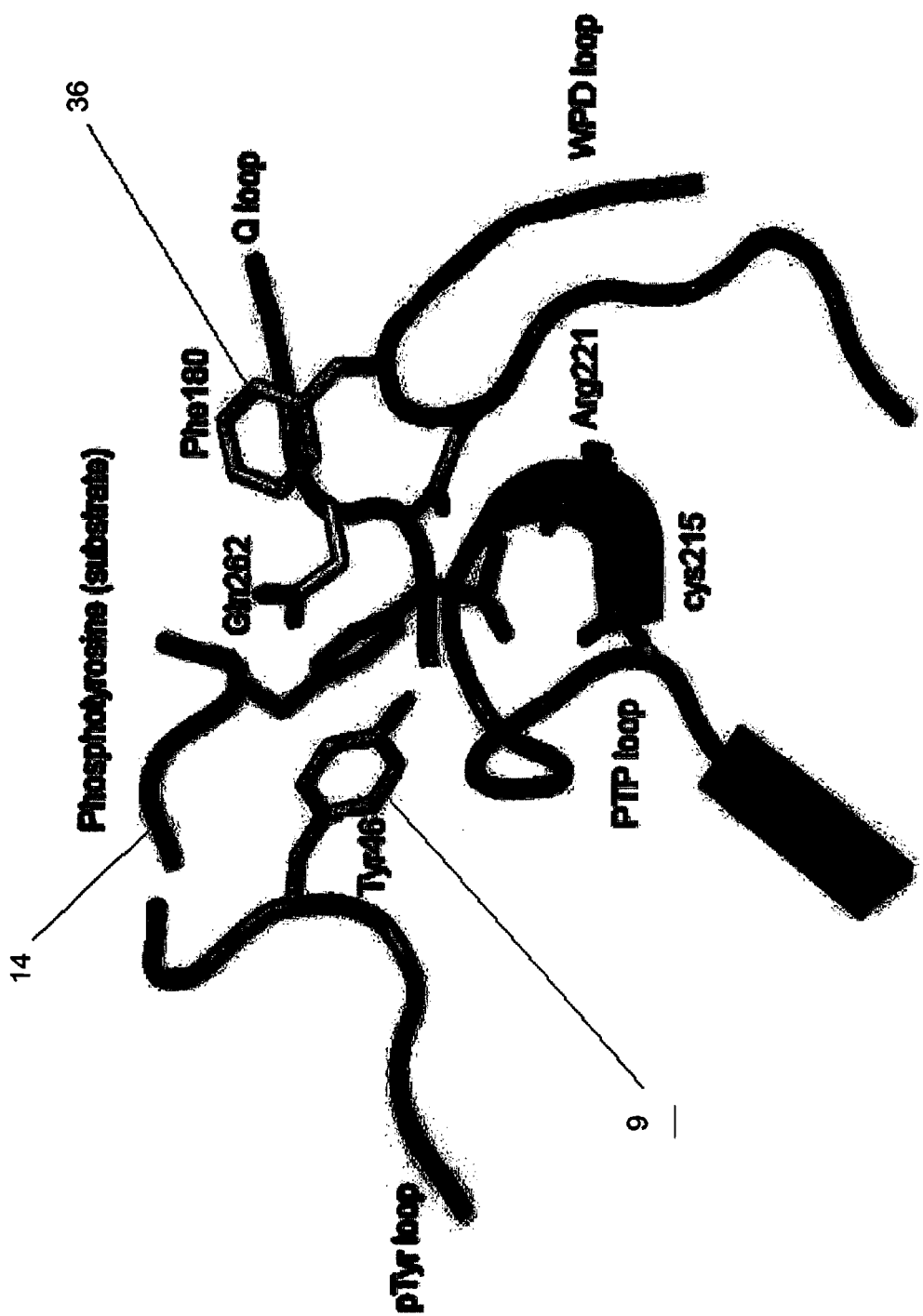
FIG. 1d depicts a representative model of the PTP1B moiety showing elements of its active site (9, 36), the substrate (14) and supporting structural elements of the protein.

In FIG. 1d, the active site of an enzyme, in this case PTP1B, is shown (e.g., 9, 36). Alternatively, molecules such as S-Nitrosoglutathione can be bound to the device and generate nitric oxide, a potent vaso dilator, using substrates from tissue surrounding the device.

The enzyme-substrate interaction is not unlike the "lock and key" analogy above and is sensitive to bond angles and the ability of the substrate to "get into the right position". This sensitivity allows modification of the activity of the treating material by changing the local electrochemical environment. The "R" groups allow addition of sites capable of such electrochemical perturbation. FIG. 1c demonstrates that the preferred location of the linking bond of the protein to the device (e.g., a stent) is on a portion of the molecule remote from the receptor-binding site of the treating material (13).

Figure 2A:
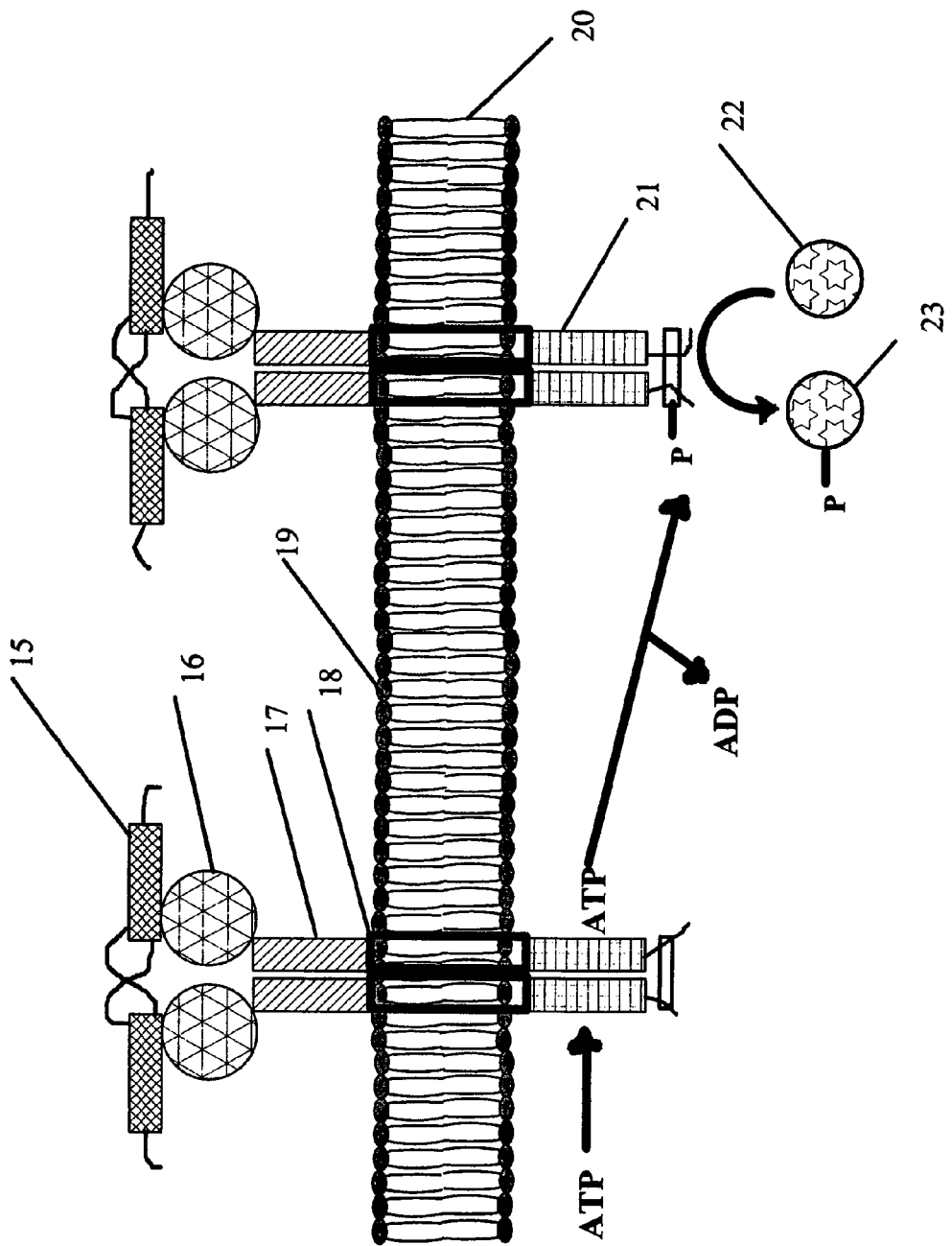
FIG. 2a illustrates the typical binding of a native growth factor, EGF (16), to the extracellular domain of the EGF receptor (17) in its dimerized state (15) during the activation of a protein kinase associated with the intracellular domain of the EGF receptor (21). The phosphorylation reaction is depicted as the transformation of target pre phosphorylation (22) to post phopsphorylation (23).

FIG. 2a is an illustration of the EGF molecule and its typical receptor-mediated activation of its protein kinase. Once the enzyme (16) and the substrate (17) become associated, the enzyme increases the probability of a chemical reaction occurring on the substrate. In this case, the reaction is the activation of the EGF receptor complex. FIG. 2a depicts a representative example of how the binding of the Epidermal Growth Factor (EGF) molecule (16) to the cell membrane based EGF receptor (17) initiates the characteristic intracellular cascade. The intramembrane portion of the EGF receptor (18) and the intracellular domain (21) are shown. Once the receptor is activated, the target molecule within the cell (22) is phosphorylated to form its product (23). Plasma membrane components, the hydrophilic domain (19), and lipid component (20) are shown for orientation.

Figure 2B:
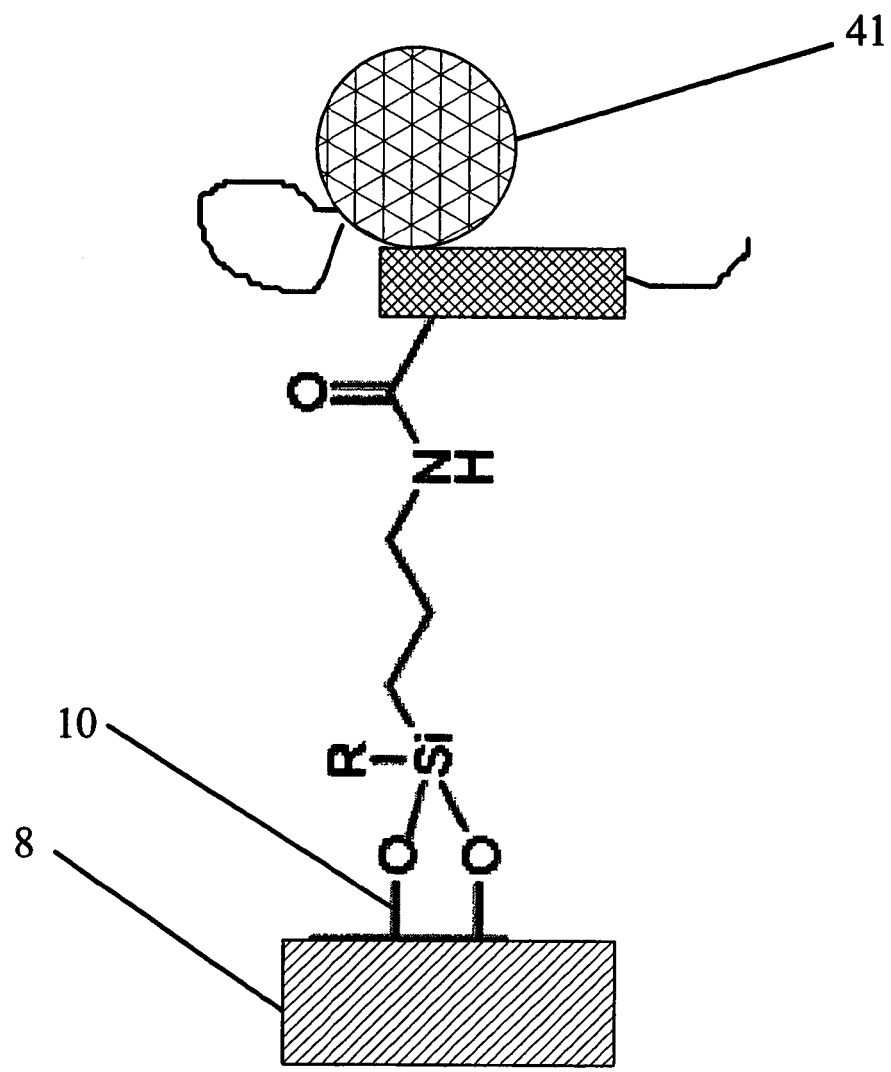
FIG. 2b illustrates a covalent linkage (10) of an EGF moiety (41) to an implantable body (8) according to one embodiment of the invention.
Figure 2C:
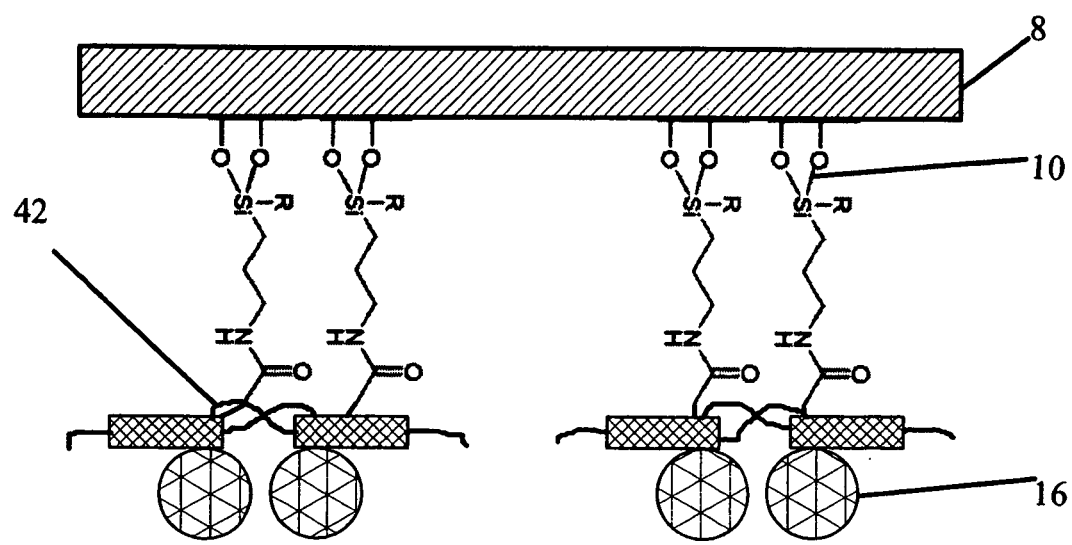
FIG. 2c depicts an arrangement of moieties mimicking the native confirmation of the dimerizied EGF molecule (42) in accordance with one embodiment of the invention. The configuration of the native molecule is reproduced on the device (8) and bound with a covalent linkage (10).
Figure 2D:
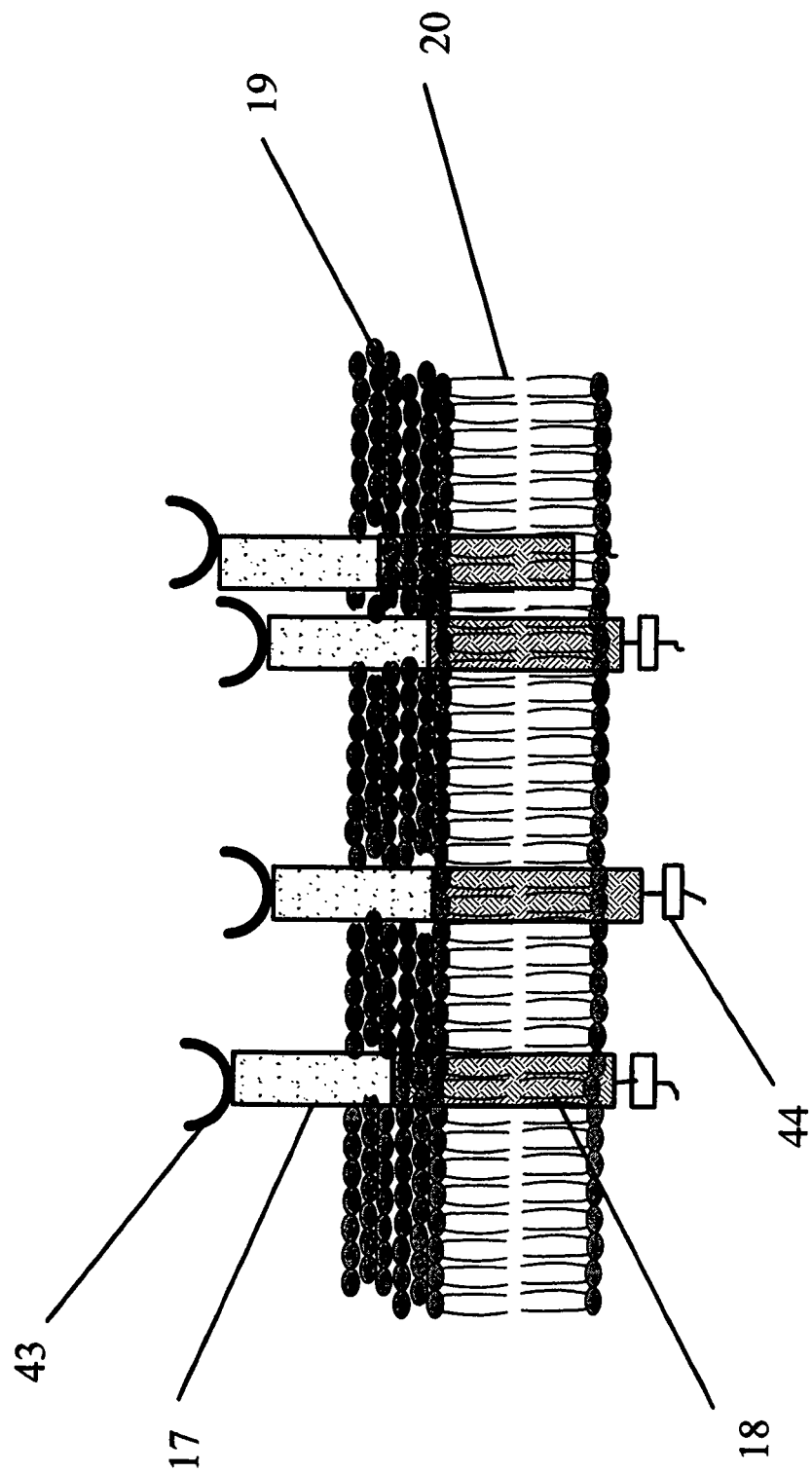
FIG. 2d represents the EGF receptors (43) floating randomly within the plasma membrane of a cell, prior to their encounter with an EGF moiety in accordance with a preferred embodiment of the invention. The phosphotydal groups (19) and lipid groups (20) are shown for orientation.

Activation of the EGF pathway can be facilitated by appropriate and non-random placement of EGF binding site homologues (41) on the device as depicted in FIGS. 2b and 2c. FIG. 2b shows binding of one such EGF moiety to the surface of an implantable body in accordance with the invention (8) using a covalent linkage (10). FIG. 2c demonstrates a substantially "native" configuration of such EGF homologues. Note the dimerized configuration of the device bound moieties (42). FIG. 2d depicts non-bound EGF receptors on the surface of a cell. The specific EGF binding site (43) and kinase (44) linked to the intracellular domain are shown.

Figure 2E:
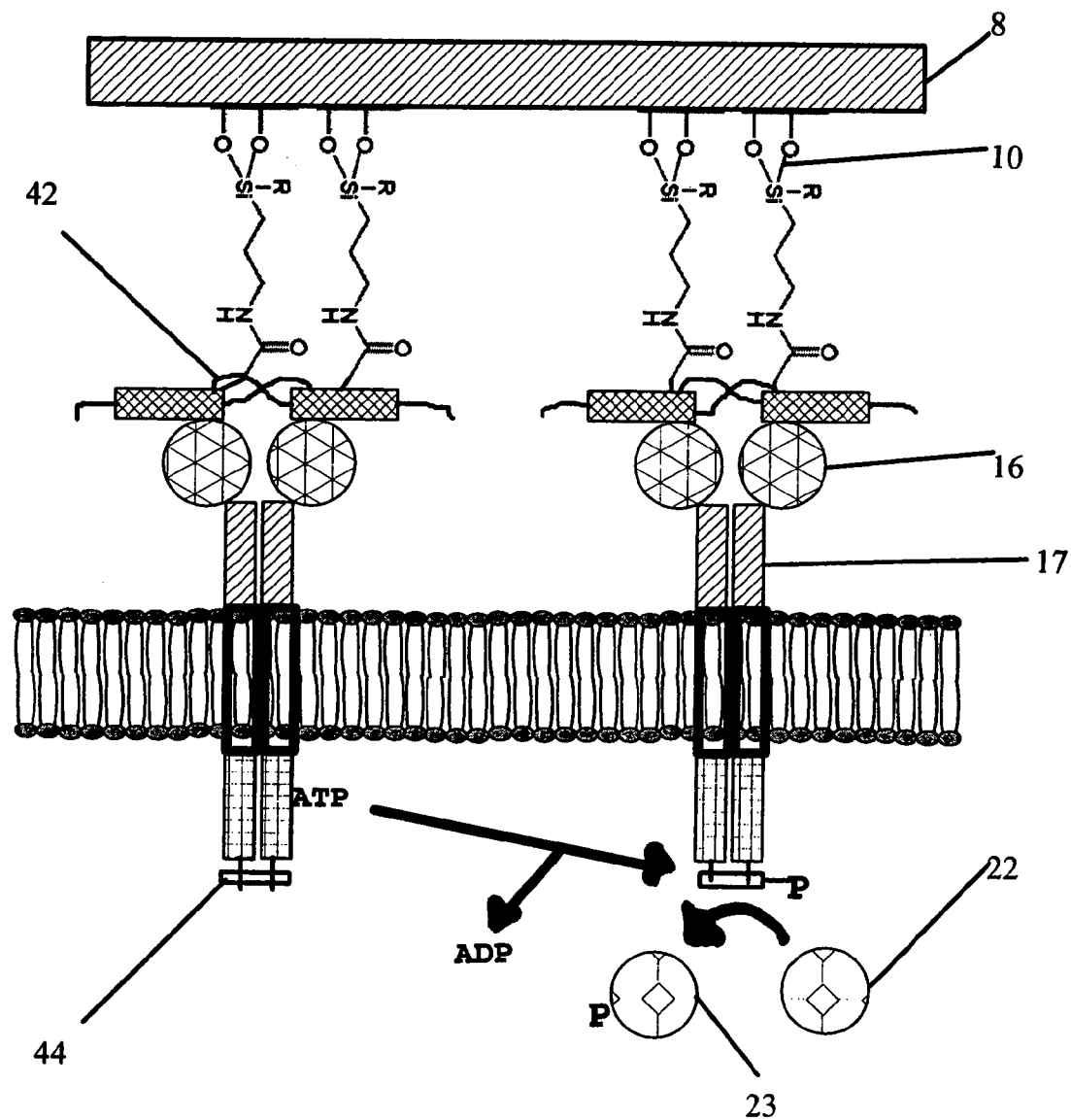
FIG. 2e represents activation of the EGF cascade by device-bound EGF moieties in accordance with one embodiment of the invention. The intracellular cascade that is triggered when a moiety, e.g., epidermal growth factor (EGF) (9), binds to its unique membrane receptor on the cell surface, thereby activating its specific tyrosine kinase (21), occurs with the exemplary device bound EGF construct.

FIG. 2e depicts the activation of the cascade by the device. After activation, the particular EGF active sites are not internalized, but are available to other receptors and/or cells. The cascade is activated as in FIG. 2a, but the EGF moieties remain linked to the surface.

By utilizing the teachings herein one skilled in the art can modify the surface of a medical device and thereby harness metalloenzyme and other complexes for use in treating disease.

The manufacturing process may include the affixation of the protein moiety to a metal reactive surface such that enzymatic activity is preserved using methods, for example, similar to those described by Cardosi et al. in the above cited reference. In this invention, the metal reactive surface can be a metal vascular stent, but also can be manufactured of any material for which a suitable substantially stable protein-device linkage can be established. For example, the device could also be produced using thin film in situ polymer enzyme immobilization. Both conducting and non conducting polymers can be used to trap the protein molecules. The use of conducting films, e.g., polypyrrole, is particularly suitable.

Covalent binding of an enzyme, nucleic acid, hormone or growth factor to the surface of the device (e.g., stent) is typically the most irreversible immobilization technique and therefore is the most preferred. In one embodiment of this invention, the chemical bonding of the enzyme to the surface is accomplished by using nucleophilic amino acid groups (e.g., carboxylic acid, hydroxyl, thiol, imidazole and phenolic groups) present on the surface of the protein that are not involved in the biological function of the molecule.

The attachment of a protein to the device may be carried out via a two-step process. First, the surface of the device can be activated, i.e., imparting some useful chemical reactivity to the otherwise inert metal surface. Second, a moiety (e.g., a protein) can be bound to the chemically activated surface of the device (e.g., the metal surface of a stent).

One exemplary synthetic scheme for immobilization of a protein molecule to a metal surface of a stent involves first the formation of an oxide on the stent surface, such as by "anodizing" the metal. Anodizing involves the electrolytic oxidation of a surface to produce a tightly adherent oxide scale which is thicker than the naturally occurring film. Anodizing is an electrochemical process during which the stent metal itself is the anode. The electric current passing through an electrolyte converts the metal surface to a durable metal oxide. The oxidized surface is hard and abrasion resistant, and provides a preferred reactive surface for this application.

Anodic coatings can be formed in chromic acid, nitric acid, sulfuric acid, phosphoric acid or oxalic acid solutions. Chromic acid anodizing is widely used to improve adhesion and reactivity. The metallo-oxide coating produced by anodizing is typically 2 mm to 25 mm thick, and comprises a thin non-porous barrier layer next to the metal with a porous outer layer that can be sealed by hydrothermal treatment in steam or hot water for several minutes. This produces a hydrated oxide layer with improved reactive properties.

The metallo-oxide then may be functionalized by a reagent such as a chloro or alkyl silane. The resulting device then may be treated with a carbodiimide-activated protein to yield a stable protein device linkage. In this example, the bond is a metaloxysilane. An exemplary scheme for this simple reaction is shown below.

The silanization reaction can be monitored using surface analysis techniques such as X-Ray Photoelectron Spectroscopy. In this case, one would detect the silanization reaction of the metal surface by noting the appearance of the new silicon and oxygen bands in the spectrum. Alternatively, one could use reflectance Fourier transform infrared spectroscopy to detect product formation, if the modifying agent contains a chromophore. To quantify the number of active sites on the surface, one can measure changes in capacitance, which result from the replacement of polar surface groups by non-polar methyl groups.

To bond an enzyme, nucleic acid, hormone or growth factor to a silanized metal surface, the organosilane reagent can bear a group of chemical functionality like a primary amine group or a carboxylic acid. A suitable reagent in this context is propyl amino silane [(CH$_3$CH$_2$O)$_3$Si(CH$_2$)$_3$NH$_2$] which will both functionalize a metal surface and then allow coupling chemistry to take place with proteins through the attendant amine group.

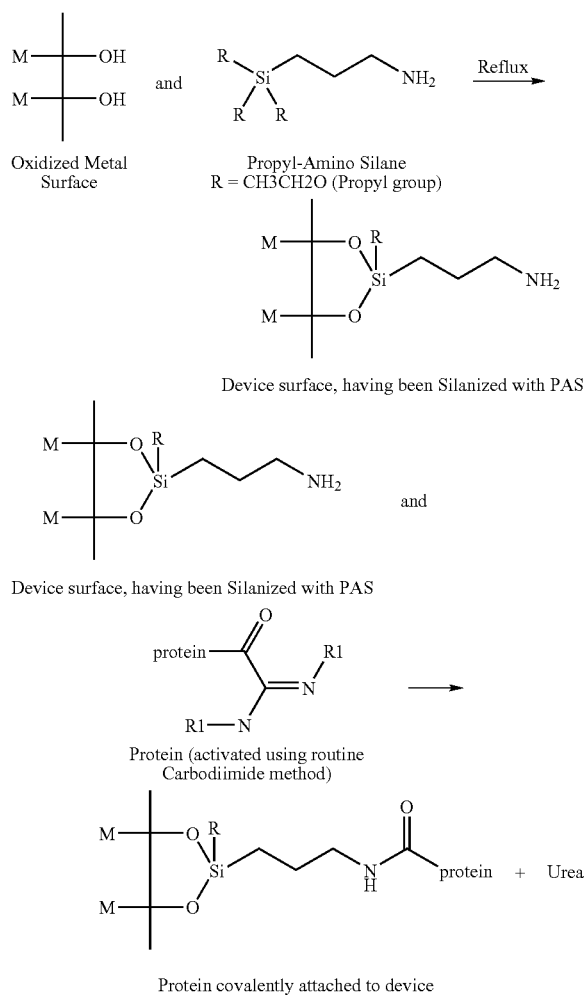

The carboxylic acid on the protein can be activated. This can be achieved by, for example, using carbodiimide chemistry. This reaction can use a variety of diimide reagents developed for solid phase protein synthesis. Suitable carbodiimide chemistry for activating the carboxylic acid of protein molecules is known in the art.

Suitable metals include platinum and gold, although these metals have not yet been used for vascular stent manufacture. Other suitable reactive surface materials include stainless steel and nitinol, metals which are used in current vascular stents. The suitability of compounds for stent manufacture can depend on the tensile and radial strength needed for a particular application, e.g., an aortic stent graft has need for a much greater surface area but has less radial strength requirement. In contrast, a stent holding open a tightly stenotic coronary artery requires high radial force distributed over a small area. The physical properties of the metallic mesh are different in these applications, yet both can be manufactured so as to covalently link active molecules to their surface as described.

Accordingly, the metallic stent or other implantable device can include at least one of stainless steel, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; a protein, an extracellular matrix component, collagen, fibrin or another biologic agent; or a suitable mixture of any of these.

If a biologically-resorbable stent material, e.g. poly(glycolic acid, PGA), is used as the reactive surface upon which the catalytic moiety is bound, the exposed [O=C—OH] PGA residues can be activated using carboxylic acid chemistry, and the support residues of the enzyme become bound covalently to the activated acid group directly upon the resorbable stent itself. Although PGA is a suitable resorbable polymer upon which this linkage can be performed, other compounds that could be used include poly(L-lactic acid), polycaprolactone, poly(lactide-co-glycolide), poly(hydroxybutyrate), poly(hydroxybutyrate-co-valerate), polydioxanone, polyorthoester, polyanhydride, poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid.

An inert surface coated with a polybiostable polymer having a relatively low chronic tissue response (e.g., polyurethanes, silicones, and polyesters), permits covalent binding of a catalytic moiety to the polymeric film. The polymeric film can be deposited on the device such as a metallic stent either by polymerization on the stent or with plasma film deposition techniques. Other suitable polymers include polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; rayon triacetate; cellulose, cellulose acetate, cellulose butyrate; cellulose acetate butyrate; cellophane; cellulose nitrate; cellulose propionate; cellulose ethers; and carboxymethyl cellulose.

Additionally, many different molecules, e.g. cofactors, can be covalently linked to an implantable device such as a metal stent, the surface of which has been activated as described above. For example, Flavin Mononucleotide (FMN) is a nonprotein catalyst which can easily be affixed to a metallic stent. The structure of FMN, shown below, has three main parts, the isoalloxazine ring, the ribitol group, and a phosphate. The isoalloxazine ring is the core part of FMN and it is the portion of the molecule which is not bound to the device surface since this part of FMN is capable of forming hydrogen bonds to the enzymes that it is associated with. The ribitol group makes up the center portion of the cofactor, while the phosphate group is bonded to the end of the ribitol. The ribatolphosphate group (an "R" group) is activated to form a silane linkage on the stent or other surface.

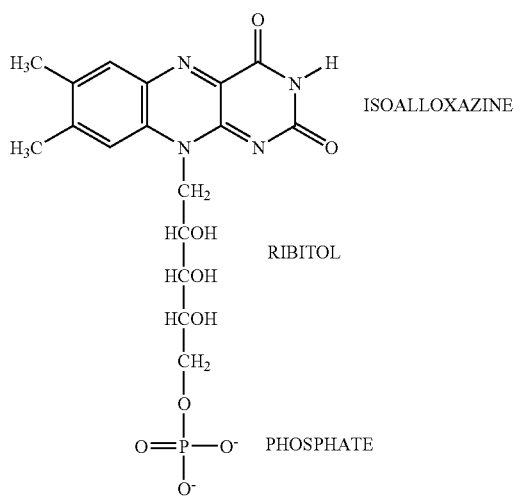

FMN can exist in any of three different redox states. When FMN is fully oxidized, it is yellow in color and absorbs energy at 450 nm. FMN can be converted to a semiquinone by a one-electron transfer. At a physiological pH, the semiquinone is a neutral radical that is blue in color and absorbs energy at 570 nm. It has a PkA of around 8.4. At higher pH values it loses a proton and becomes a radical anion, which is red in color and absorbs energy at 490 nm. When FMN loses a second electron, it is converted into a completely reduced dihydroflavin that is colorless.

Since FMN is able to convert into these three different redox states, it can participate in one-electron transfer and two-electron transfer reactions. Because of these properties, FMN is able to catalyze a wide array of reactions, and also work with many other electron donors and acceptors. Reactions catalyzed by FMN include, for example, two electron donor/acceptors like NAD+ and NADPH+, one or two-electron carriers like quinones, and one-electron donor/acceptors like cytochrome proteins. The only requirement for incorporation of a cofactor such as FMN onto a surface such as a stent is that an activated group on the molecule (in the case of FMN, the ribatylphosphate group) is bound to the stent remote enough from the "active site" (in FMN, the isoalloxazine moiety) so as not to interfere with its catalytic function.

The chemistry of activated phosphate groups such as the ribatylphosphate group of FMN has been used to explore intermediates in protein synthesis (see "Activation of Acyl Phosphate Monoesters by Lanthanide Ions: Enhanced Reactivity of Benzoyl Methyl Phosphate," Ronald Kluger and Lisa L. Cameron *J. Am. Chem. Soc.* 2001 124:3303-3308, and "Biomimetically Activated Amino Acids. Catalysis in Hydrolysis of Alanyl Ethyl Phosphate," Ronald Kluger, Richard W. Loo, and Vince Mazza, *J. Am. Chem. Soc.* 1997 119 12089-12094). Activated phosphate group chemistry is also suitable for the coupling of activated phosphates to reactive surfaces, in particular metal oxides formed on the metallic stent used in preferred embodiments of this invention. The formation of the activated metal oxide, e.g., by "anodizing", on the stent surface, is discussed. Various techniques can be used for protecting functional groups distant from the desired covalent linkage point. (See, e.g., Protective Groups in Organic Synthesis. Theodora W. Greene, Peter G. M. Wuts, 3rd Edition, June 1999 ISBN: 0-471-16019-9—John Wiley & Sons Inc, hereby incorporated by reference in its entirety).

The incorporation of an enzyme, nucleic acid, hormone or growth factor onto a surface can ultimately be monitored by challenging the surface with the substrate of the enzyme and subsequently detecting the production of an electrochemical product or absorption of a characteristic wavelength of energy.

Figure 3A:
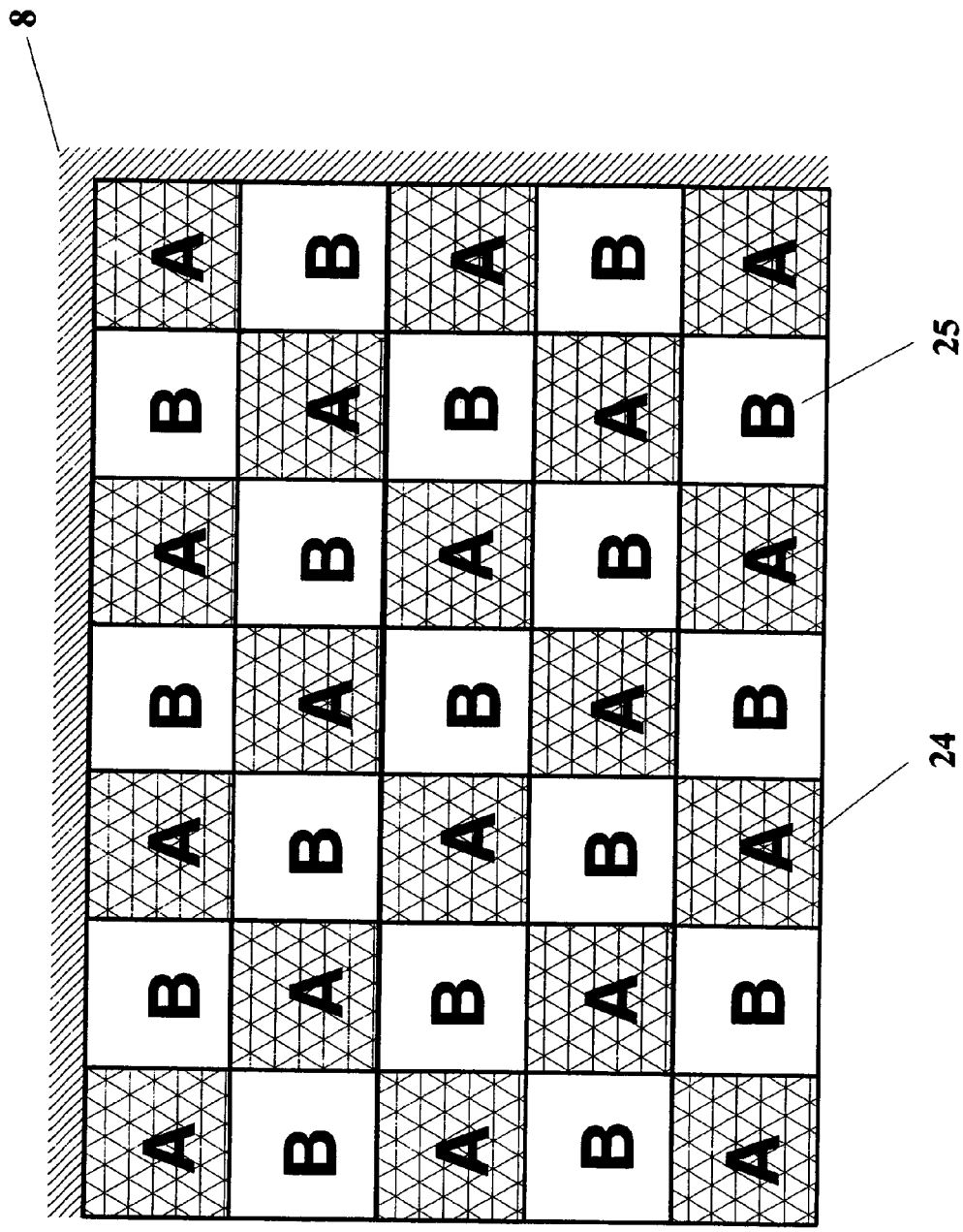
FIG. 3a illustrates exemplary blocks of two different moieties, (e.g., enzymes, hormones or growth factors) arranged on the same device in a matrix in accordance with a preferred embodiment of the invention.
Figure 3B:
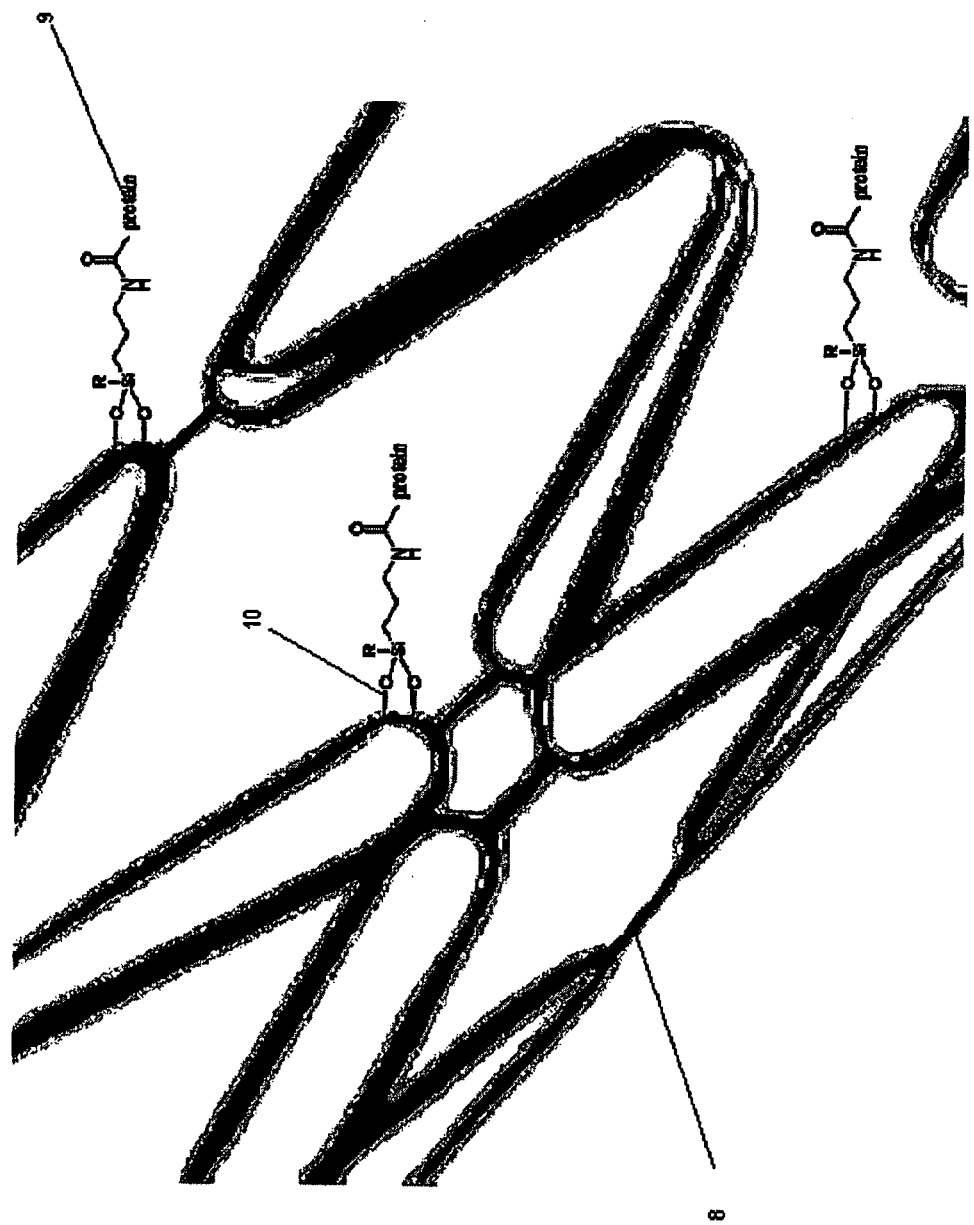
FIG. 3b depicts a magnified view of an exemplary device according to a preferred embodiment of the invention in the form of a vascular stent.

FIG. 3a demonstrates bonding two enzymes to a device in an alternating "checkerboard" pattern. When more than one biologically active molecule is bound to the surface (8) at the same time, different reactions can be catalyzed by a single device. This arrangement is depicted in FIG. 3a. In this case, two different treating materials "A" (24) and "B" (25) have been bound in a "checkerboard" array. FIG. 3b shows three different moieties used on the same device. The third "C" (26) is shown. To accomplish this patterning of different moieties, masking and etching techniques of printed circuit design may be employed to "protect" some areas of the metal, while letting others react. Referring back to the discussion of preparing the bare metal stent for protein binding, oxidation of the metal may be employed prior to initiation of the silane reaction. Differential binding of protein moieties may similarly be achieved by protecting some regions of the metal from the oxidation reaction, while letting other regions oxidize. Any suitable reagent may be used to prevent metallic oxidation. Various agents have been used in rust (iron oxide) protection on bridges and automobiles. This invention makes use of these and similar methods on the surface of a medical device to selectively bind different protein moieties using an oxidation reaction as outlined above.

FIG. 3b shows a vascular stent manufactured in accordance with an embodiment of the present invention. Note that in this illustration the treating material (9) has been bound to the stent (8) by a non hydrolysable silane linkage (10). In this particular embodiment, the stent surface has been uniformly treated such that a single enzyme, nucleic acid, hormone or growth factor moiety is uniformly bound to its surface.

Figure 3C:
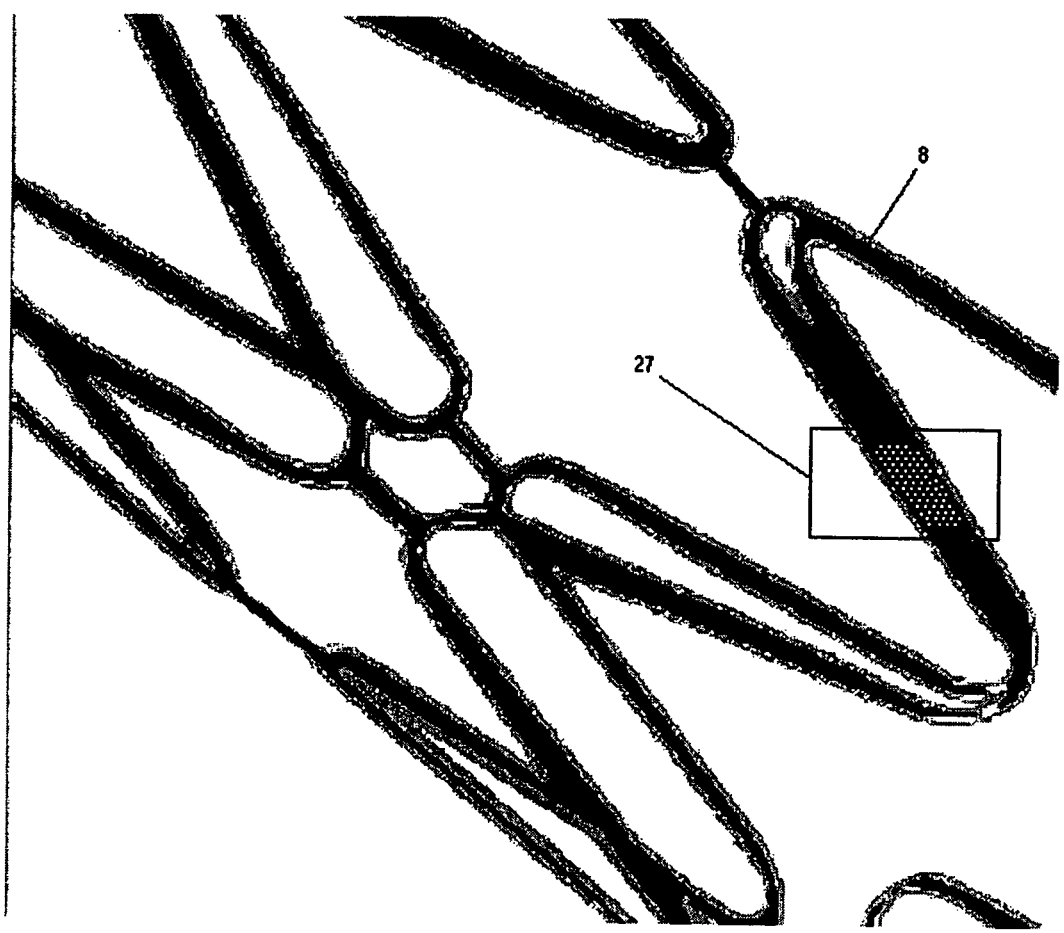
FIG. 3c shows a lower power view of the arrangement of FIG. 3a (27) placed on a vascular stent (8) in accordance with an embodiment of the invention.
Figure 3D:
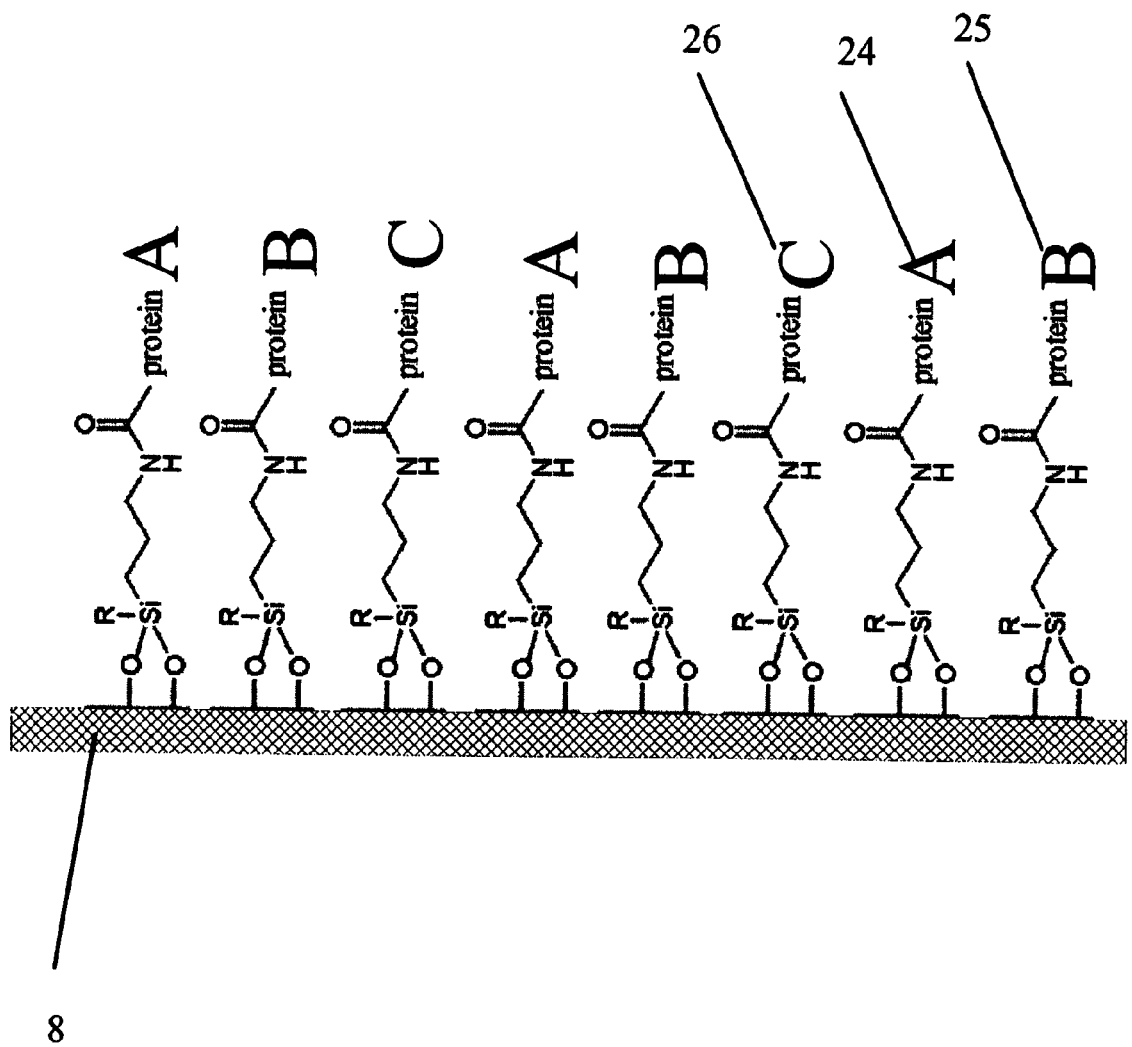
FIG. 3d illustrates a device according to an embodiment of the invention having three distinct active moieties labeled "A", "B", and "C", affixed to the device surface using non-hydrolysable bonds (10) arranged in a linear manner.
Figure 4A:
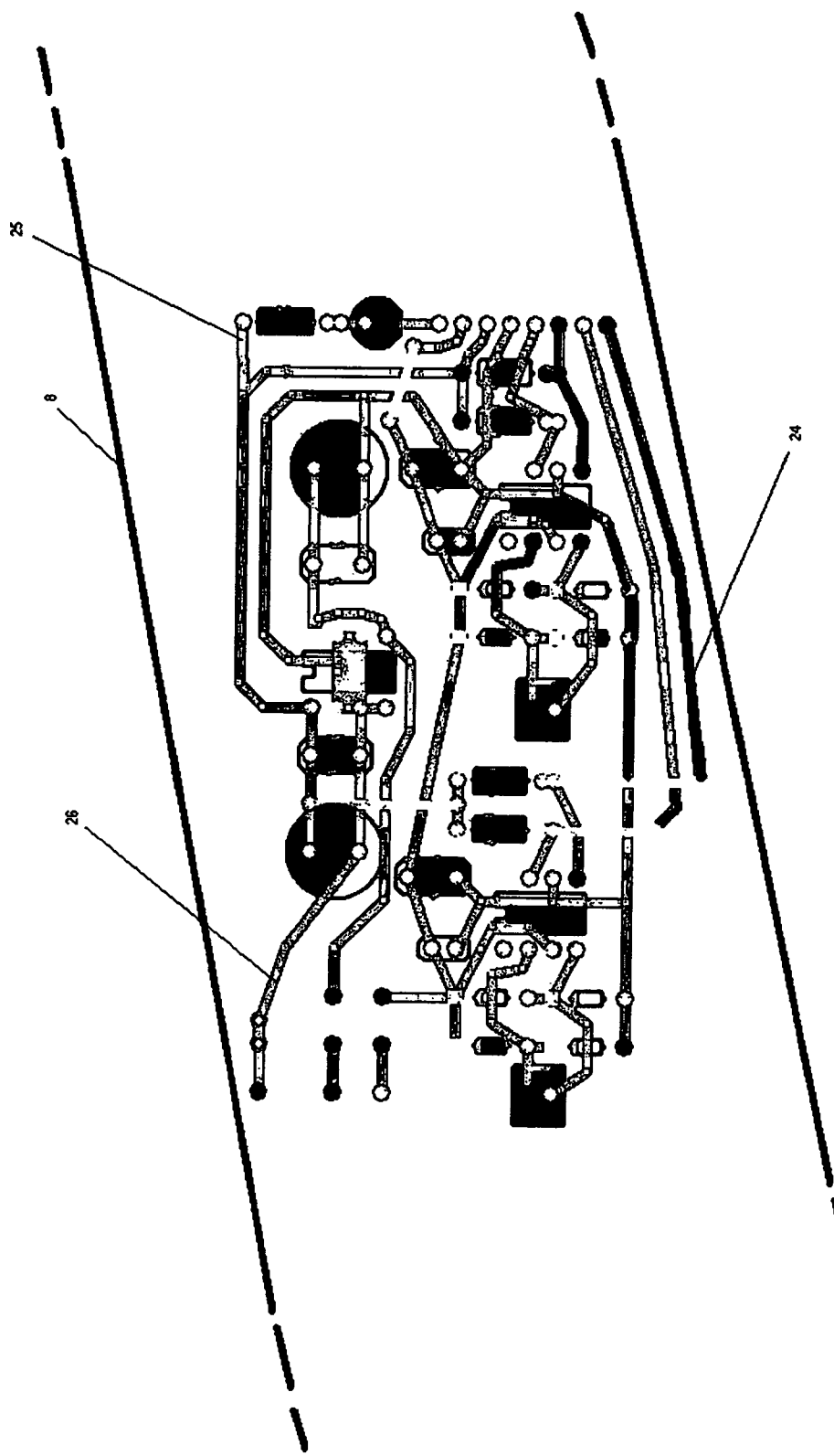
FIG. 4a depicts an array of active moieties, e.g., enzymes, hormones or growth factors, on the surface of a device according to an embodiment of the invention.

FIG. 3c depicts a "checkerboard pattern" on the surface of a stent. The box (27) represents the area shown as a magnified view in FIG. 3a. The pattern of treating materials on the surface of devices according to the invention can be made more intricate, such as that typically encountered in an electronic printed circuit as depicted in FIG. 4a. In FIG. 4a, the patterning of enzyme moieties as depicted above is laid down in a more complex circuit arrangement (11). Note that the circuit here shows an arrangement of treating materials "A" (24), "B" (25), and "C" (26). This pattern is on the surface of a vascular stent (8) in accordance with another embodiment of the invention. FIG. 4b represents a low-power view of the circuit surface (11) of such a stent (8) made in accordance with the invention.

Thus, in one embodiment, protein molecules are laid down in the pattern of an electric circuit. The ability to use the platform upon which the enzymes, hormones or growth factors are bound as a conductor of electricity permits the addition of externally applied energy to the system after the device has been deployed. Current generating devices that convert applied energy from a distance into local electric current are known. Photocells, as simple as those on the common calculator, have now been converted to sub-millimeter sizes. Photocells with the light receiving area of only 0.5 mm×0.5 mm are capable of supplying enough power to drive a commercially available DC motor using only laser irradiation. Similar cells may be used in embodiments of the present invention to modify device activity after deployment.

Figure 5A:
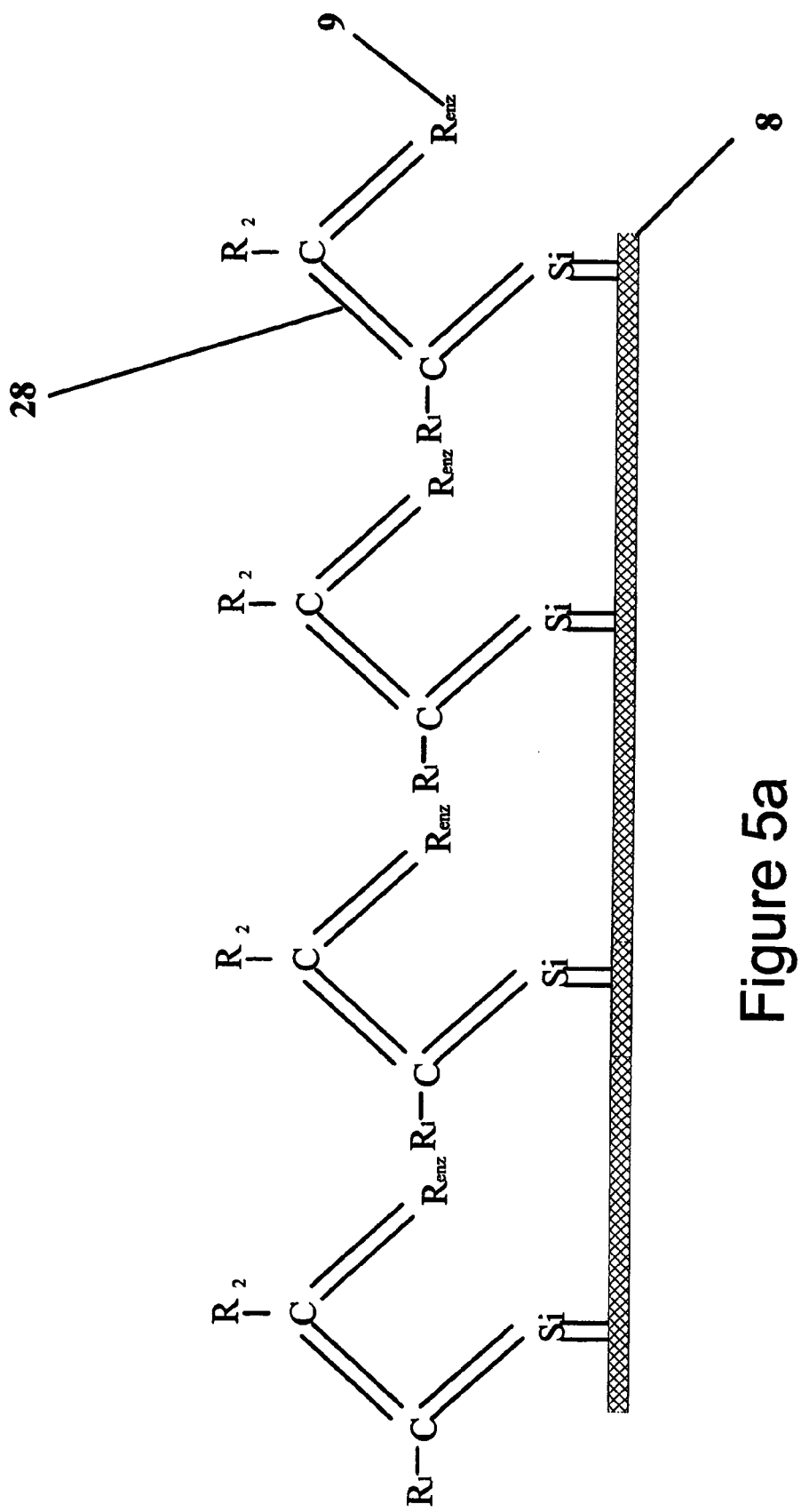
FIG. 5a depicts a series of moieties such as enzymes that are in the cis-configuration (28) on a device according to an embodiment of the invention.
Figure 5B:
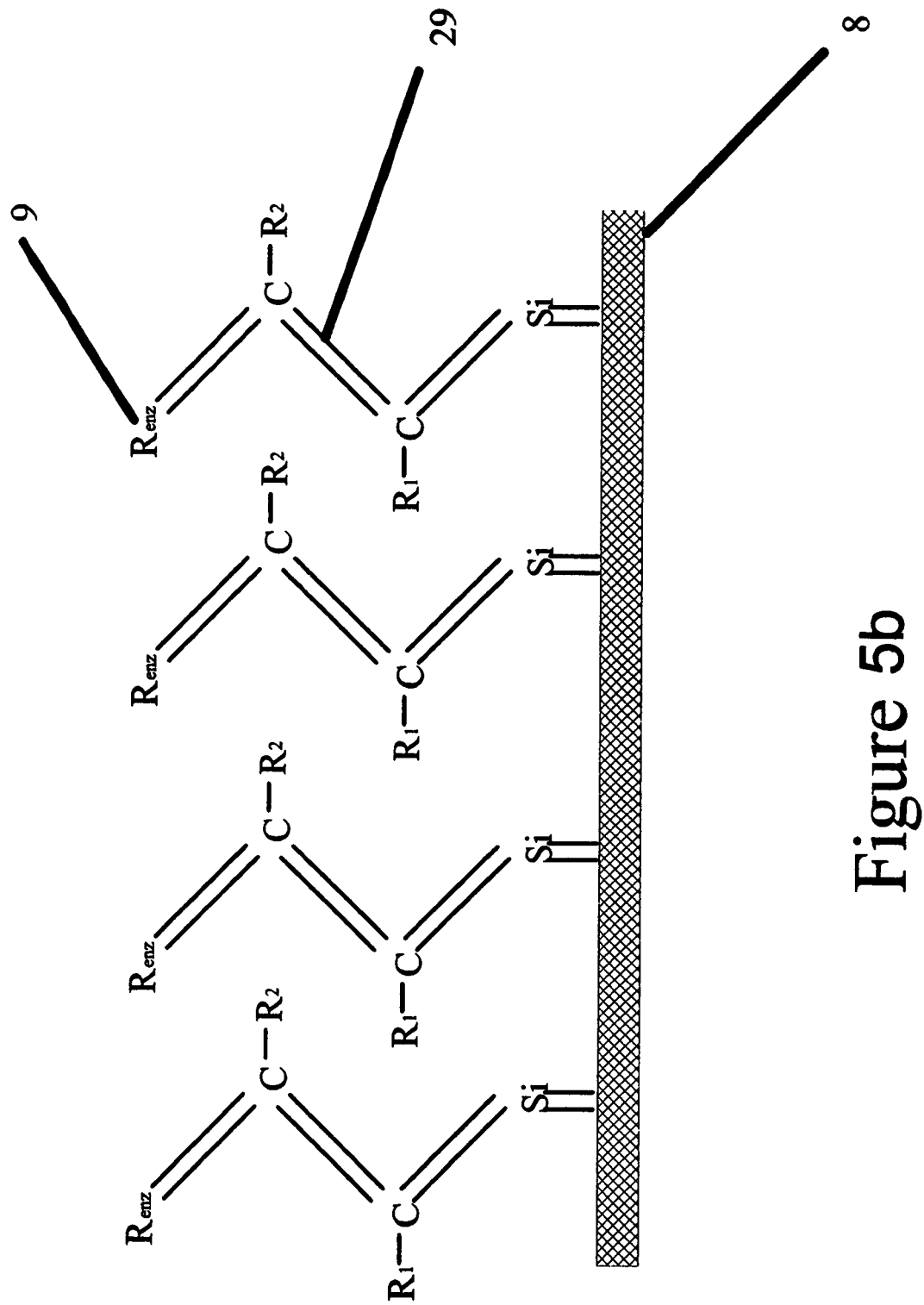
FIG. 5b shows the series of moieties such as enzymes of FIG. 5a in the trans-configuration (29) on a device according to a preferred embodiment of the invention after receiving a pulse of externally applied energy.

FIGS. 5a-b illustrate such a transformation. If the bonds originally holding a particular moiety to the metal are in cis configuration (28), as shown in FIG. 5a, they can be converted to trans (29) which, shown in FIG. 5b, are more thermodynamically favorable, if given a pulse of externally applied energy with the correct wavelength.

Any suitable compounds may be used to produce the photoelectric effect. Titanium Dioxide ($TiO_2$) and silver are suitable compounds. $TiO_2$ is a desirable photovoltaic material because of its large band gap, i.e., the potential energy between the conducting and valance levels of the material. In the photoelectric effect, photons with energies greater than the band gap potential excite the electron on the surface of the material from the valance level to the conducting level. This excited electron is now free from the lattice and able to do work in an external circuit. Visible light does not have enough energy to excite the electrons in titanium dioxide, but $TiO_2$ can be associated with a dye material that is photo-reactive in visible light. Silver (Ag) is a material that is photo-reactive in visible light. This agent will eject an electron when excited, which will then excite an electron on the $TiO_2$. Ag has a relatively high absorbency and at the same time it covers a broad portion of the wavelengths in visible light.

Photoisomerizable molecules undergo reversible structural changes when exposed to specific energies of light or other forms of applied energy. Their two states often differ considerably, for instance in their conformation, local charge, polarization or shape. Since the spatial relationship of the active site of an enzyme with the substrate is the basis for enzyme function, photoisomers can be used to alter this relationship and thereby alter enzyme function. An irreversible physical or chemical change is a reaction that will not spontaneously reverse itself without some change in the surrounding conditions, such as the addition of energy. Perturbations of the local electrochemical environment can change thermodynamic equilibrium such that the enzyme will cease to work properly. As the substrate molecule comes into contact with the enzyme's active site, it forms temporary hydrogen bonds with the enzyme. These bonds can only form if the active site of the enzyme is exposed appropriately to the substrate. If the active site is not exposed appropriately, the reaction has a much lower probability of occurring. The hydrogen bonds formed between enzyme and substrate during the establishment of the enzyme-substrate complex are sensitive to bond distance and other features of the "lock and key" analogy. By applying pulses of energy as described herein, one can change the local thermodynamic equilibrium such that an enzyme will cease to bind to its substrate.

Consequently, when an enzyme molecule is functionalized with photoisomerizable groups, the local environment of the active site of the enzyme can be changed as a result of changes in the confirmation of the photoisomerizable moiety. The activity of the enzyme may thus be controlled by the input of energy, for example, by strobe application of light. Applications using various enzymes, e.g., Cytochromes, NAD, and FAD, and nucleic acids, e.g., RNA, and using different forms of stimulation, e.g., electrical, laser light, and magnetic, have been performed in vitro results (see, e.g., Willner and Willner, *Pure Appl. Chem*, (73) 535-542, 2001, for a recent review). The present invention, in contrast, teaches in one embodiment a device using a circuit of such enzymes on an implantable device made of an electrode-like substance in vivo, and the subsequent modification of reactions of the neighboring cells and fluid in and around the site of implantation by the application of external energy, e.g., laser light, or alterations of local magnetic field through the skin or from tissues adjacent to the device.

Example 1

Modification of Enzymes In Vivo

Laser light, for example, the Helium-Neon (HeNe) laser, may be used for transillumination of the skin in medical practice. According to an embodiment of the present invention, laser such as HeNe laser activation of a microphotocell is used to induce alterations of enzyme activity on the surface of an implantable medical device in vivo.

An enzyme, having been linked to a suitable reactive surface as described above, is first modified with photoisomerizable "R" groups.

Although there are numerous molecular bonds that change configuration following external stimulation, a representative example is the conversion of a cis to a trans covalent linkage. The best characterized of the photosensitive cis-trans linkages are the Azobenzine Photoisomers.

Synthesis of an Azobenzine Moiety 4,4-Diaminoazobenzene (0.24 mmol) (Lancaster Synthesis) is dissolved in anhydrous tetrahydrofuran (10 ml) and is stirred under nitrogen for 15 min, protected from light. Three equivalents of triethylamine (0.70 mmol) are then added, followed by three equivalents of chloroacetyl chloride (0.70 mmol, dropwise). The reaction mixture is then to be filtered and the solvent evaporated. Sodium iodide (26 mmol) is then dissolved in anhydrous acetone (16.25 ml) with anhydrous tetrahydrofuran (5 ml) (degassed) and is then added to the reaction flask. This mixture is stirred for 18 h under nitrogen, protected from light. It is then filtered to remove NaCl, and the solvent is then removed to give a brownish/yellow solid. The solid is then redissolved in tetrahydrofuran (2 ml), and excess NaI removed by filtration. To the tetrahydrofuran solution, ice-cold water is then added in 1-ml increments until a precipitate forms (3 ml $H_2O$).

Coupling of the Azobenzine Moiety to a Protein

Various processes of linking a peptide segment to an Azobenzine ring may be used. A method well suited for this is that of Kumita et al. (Kumita, J. R., Smart, O. S. and Woolley, G. A. (2000) *Proc. Nat'l Acad. Sci. USA*, 97, 3803-3808).

Photoisomerizable "R" groups are also well suited to use in this invention. Photoisomerizable "R" groups are not limited to spiropyran and merocyanine derivatives and include the amino acid phenylazo-1,2,3,4-tetrahydro-3-isoquinolinecarboxylic acid (PATIC), nitrospiropyran carboxylic acid derivatives, pyridine thiol derivatives, and nitrospiropyran thiol derivatives.

Whichever of the methods used to couple the peptide moiety to the photoisomerizable molecule, or if a new method of energy-sensitive conformational change is developed, the invention calls only for the coupling of such a moiety to a catalyst or cofactor such that catalytic activity can be regulated by application of external forces resulting from a change of the physical properties of the photosensitive group.

Example 2

Device as Platform for Photosensitive Enzyme Expression

Once a photosensitive moiety has been bound to the catalyst (9), and the catalyst upon the stent (8), the resulting device exhibits photoisomer-controlled enzymes on the surface, the activity of which can be modified externally after the device is deployed. The mechanism of external stimulation of the "R" groups is not critical, e.g., direct photoactivation, alteration of local voltage by applied electrons, alteration of the local redox environment, or variance of local magnetic field, except that it be under suitable control by the medical practitioner.

Figure 6A:
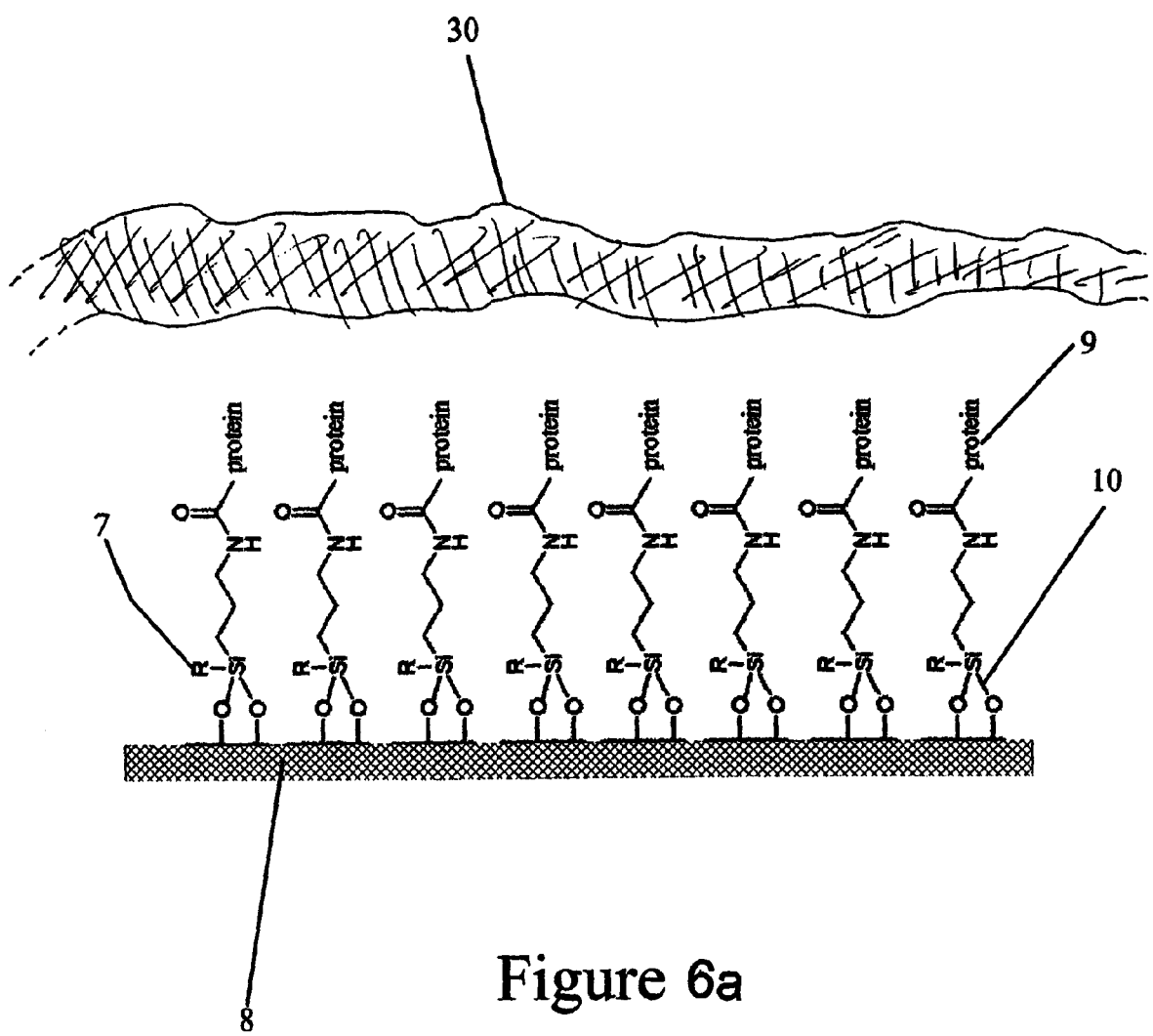
FIGS. 6a-b illustrate embodiments of a method of protecting some or all of a device according to an embodiment of the invention from direct fluid/tissue contact for a specified period of time.
Figure 6B:
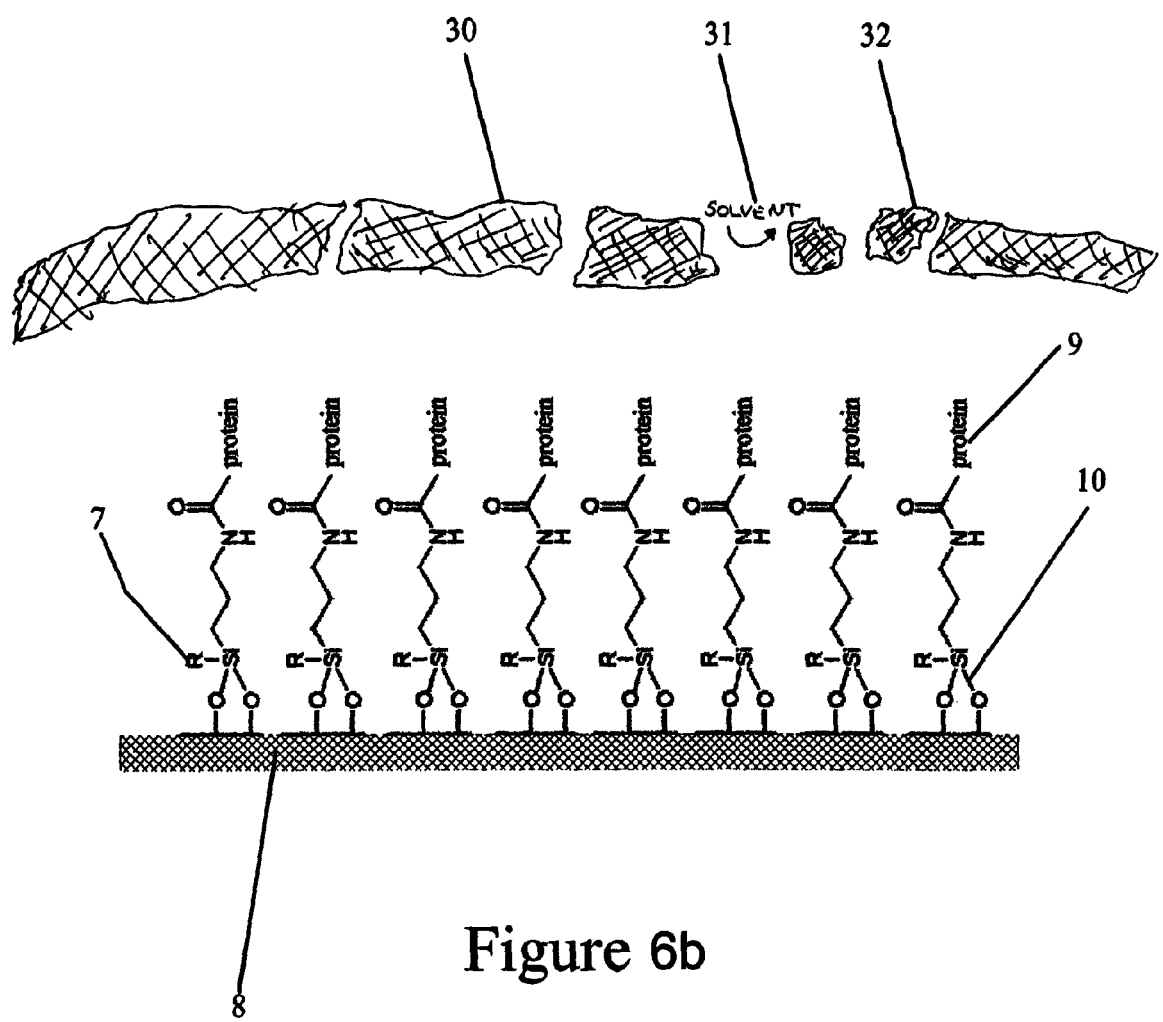

Selective Activation of Some Surface Enzymes Preferentially by Means of an Intrinsic Circuit In addition, applying energy selectively to parts of the "circuit (11)" and not to others allows the operator to selectively change the local thermodynamic environment of some enzymes but not of others. Because one can change the activity of enzymes in solution by the application of electric current as taught herein, the practitioner can differentially alter the local electrochemical milieu of an enzyme, nucleic acid, hormone or growth factor. As taught herein, such conformational charge can effectively "turn off" the enzymatic activity by application of suitable energy. This is due to the "refolding" of the protein in response to changes in its local thermodynamic equilibrium, e.g., some exposed amine or hydroxyl groups having attracted additional free protons from solution. The entire device can be protected from damage to these functional groups during deployment or for a period of time after deployment, if desired, by precoating the device with a degradable polymer (FIG. 6a-b).

Protection of Enzymatic Moieties Prior to Activation

In the embodiment of FIG. 6, the active sites (9) of the treating material are covered with a protective coating (30) prior to deployment. Upon administration of an appropriate solvent (31), the coating will erode. The solvent is not limited to water, but could include any hydrolytic enzyme released from cells, or administered to the patient, or into fluid bathing the device. During dissolution, fragments of the protective coating (32) are released into solution by the dissolution reaction. The active sites are then free to perform their function.

The Invention as a Means for Activation of a "Molecular Switch"

The application of external energy thus provides the invention with a "molecular switch" to turn on or off specific enzymatic activities based on the pattern of applied energy from, for example, a helium-neon laser, which has already been documented safe for medical purposes.

Figure 7A:
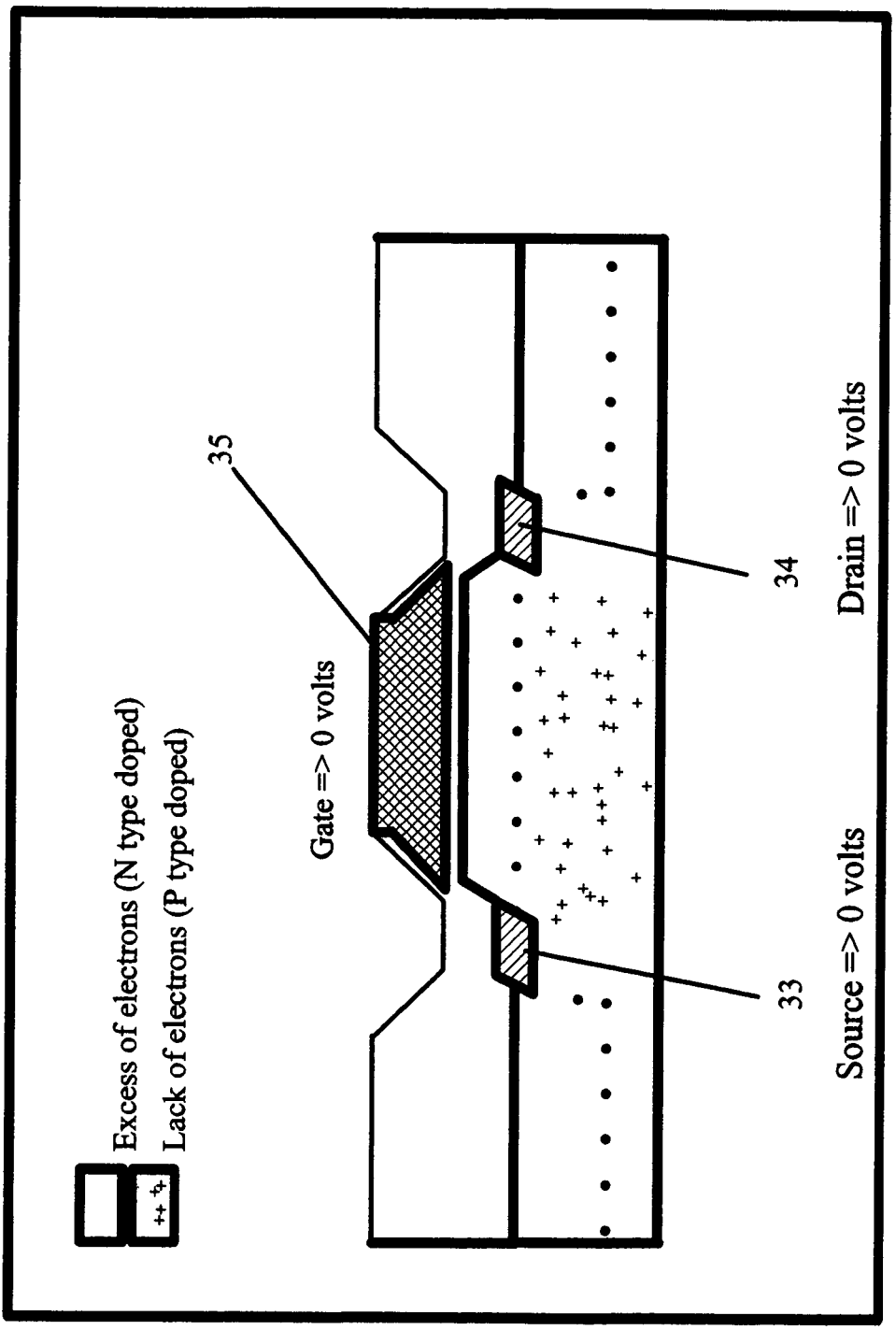
FIGS. 7a-d depicts a three layered device according to another embodiment of the invention.
Figure 7B:
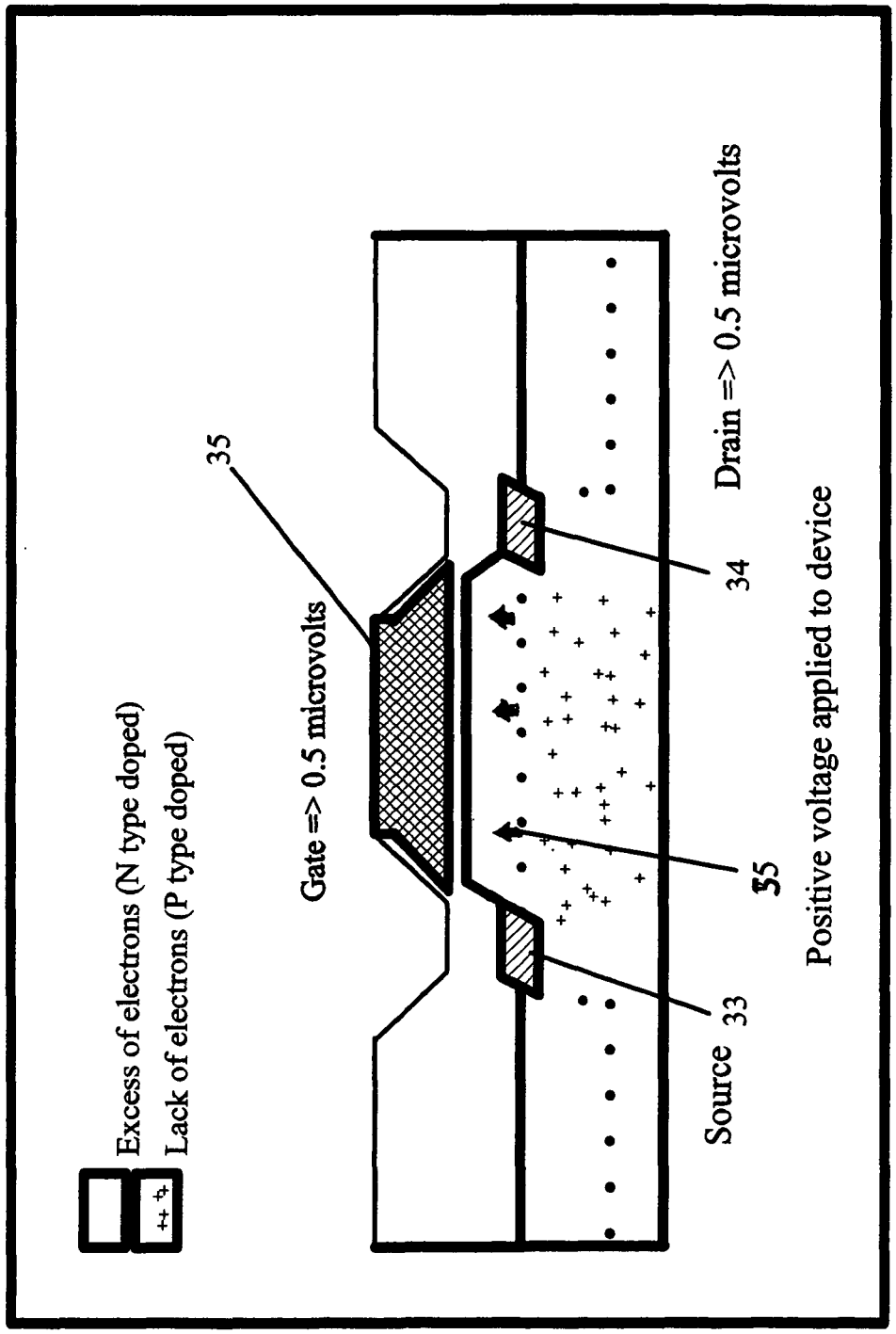

FIGS. 7a-d depicts how, when the device is manufactured as a three layered device with suitable circuitry, the stent or other implantable device can resemble a semiconductor. Note that the "LCD" output function is performed by an array of enzymes, hormone or growth factors on the surface of the device. A complex series of enzymatic activity profiles can be choreographed by a microchip on the surface of the device if stimulated appropriately. In FIG. 7a, the classic transistor elements are shown. The source (33), the drain (34), and the gate (35) are illustrated. In FIG. 7a, no applied voltage is present. In FIG. 7b, however, positive voltage is applied (55).

Figure 7C:
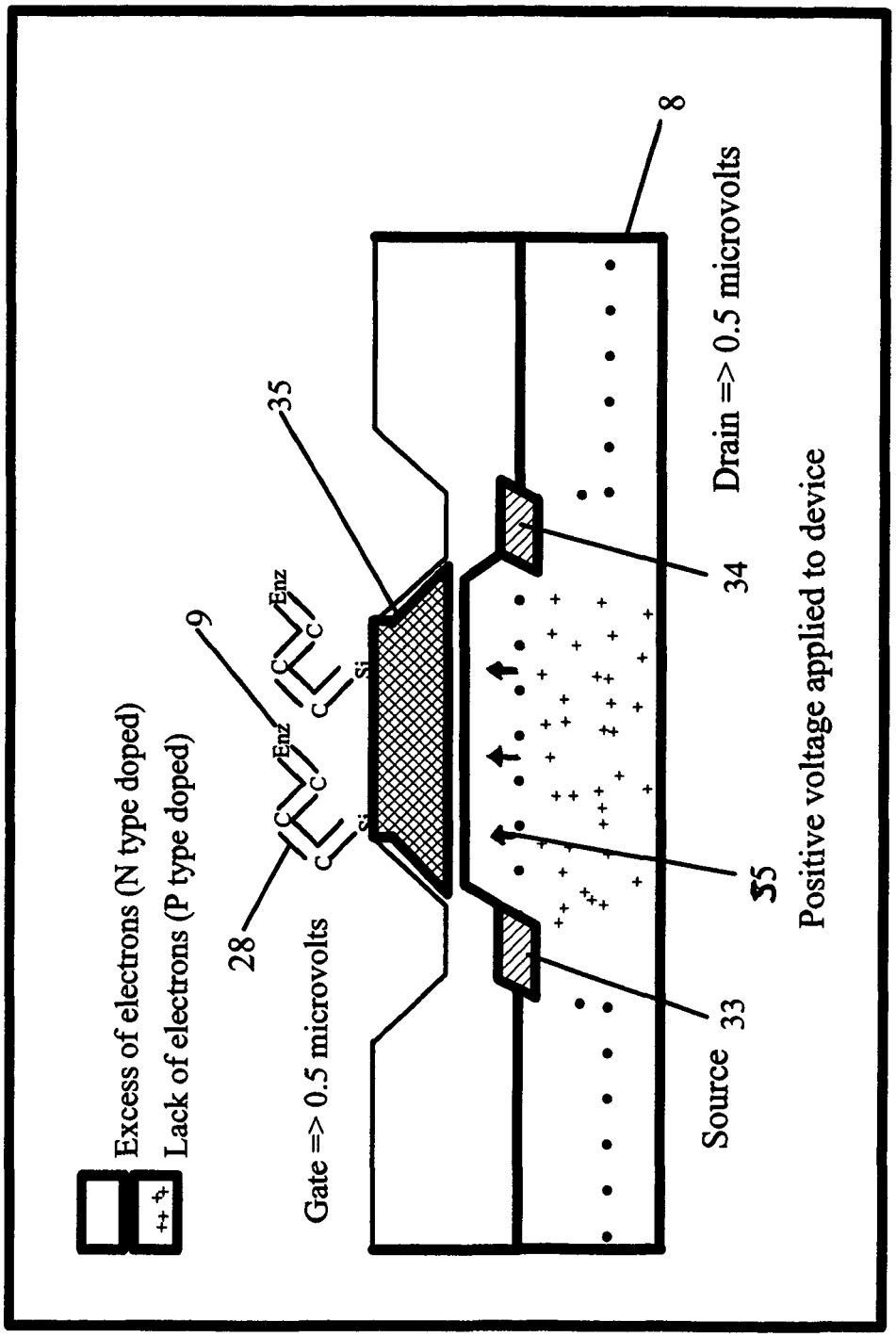
Figure 7D:
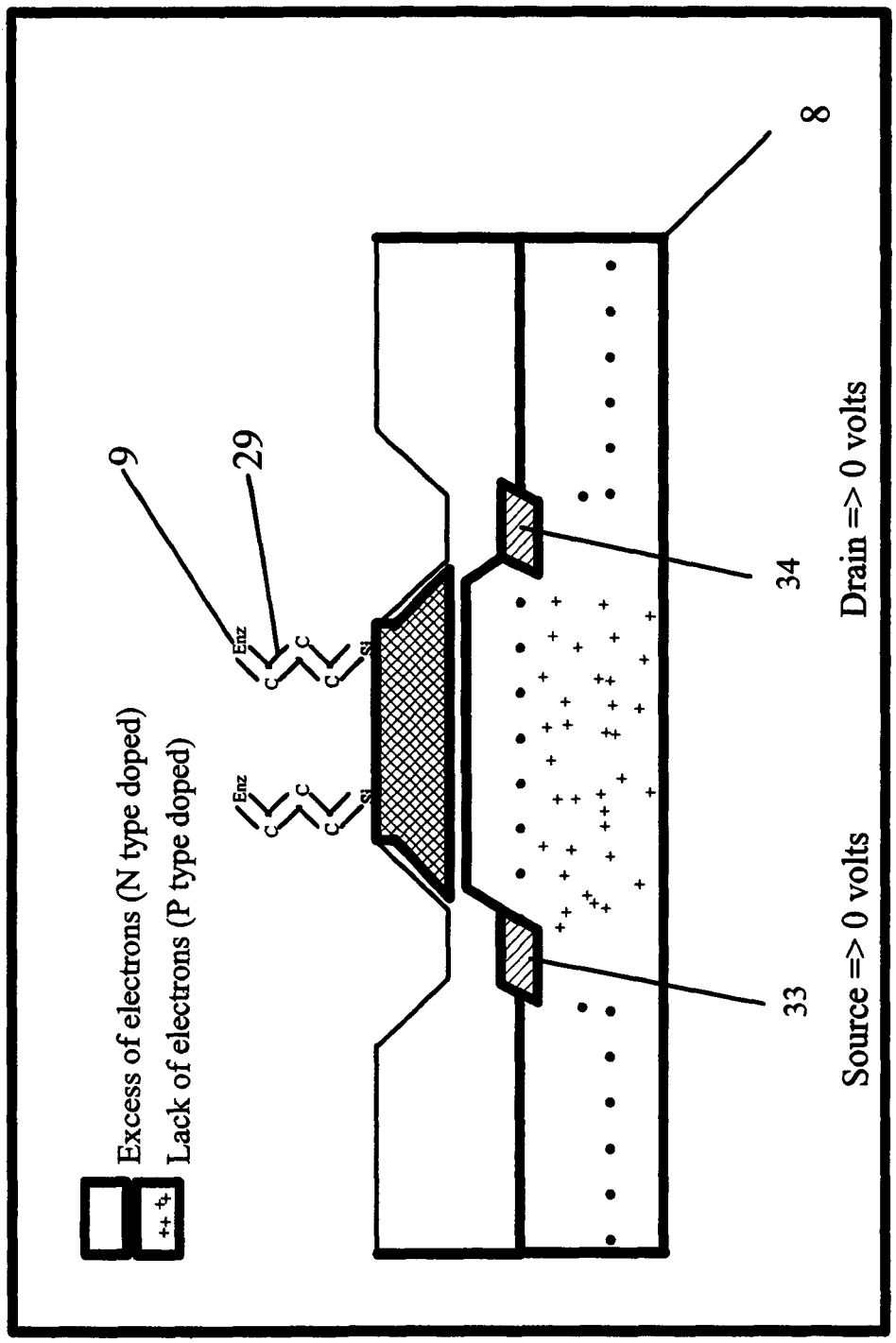

Note that current flows through the gate (35). In FIG. 7c, a representative effect on enzyme moieties (9) attached to the device surface (8) following application of current (55) is shown. Note that in the case of positively applied voltage, the more thermodynamically unfavorable cis configuration (28) is achieved. The crowding of active sites makes them "inactive" in this example. FIG. 7d shows the enzyme moieties more exposed as a result of the cessation of applied energy and the subsequent relaxation of the cis bonds to trans (29).

Example 3

Vascular Stent

This invention addresses, in one embodiment, the use of hydrophilic compounds in the prevention of restenosis. A review by Christopher J. Molloy in *Current Pharmaceutical Design*, Volume 3, Number 6, outlines numerous hydrophilic polypeptide growth factors and vasoactive G-protein-coupled receptor (GPCR) agonists. Examples of the former, such as platelet-derived growth factor (PDGF), bind to and activate cell surface receptor tyrosine kinases, initiating intracellular biochemical signaling pathways associated with cell proliferation or migration. In contrast, vasoactive GPCR agonists, e.g. angiotensin II (AII), endothelin-1 (ET-1), alpha-thrombin, may elicit cell growth indirectly by inducing the production of autocrine or paracrine factors in vascular cells. These factors have thus far been of limited use clinically largely because of the inability to restrain these hydrophilic molecules at the site of injury.

Figure 8A:
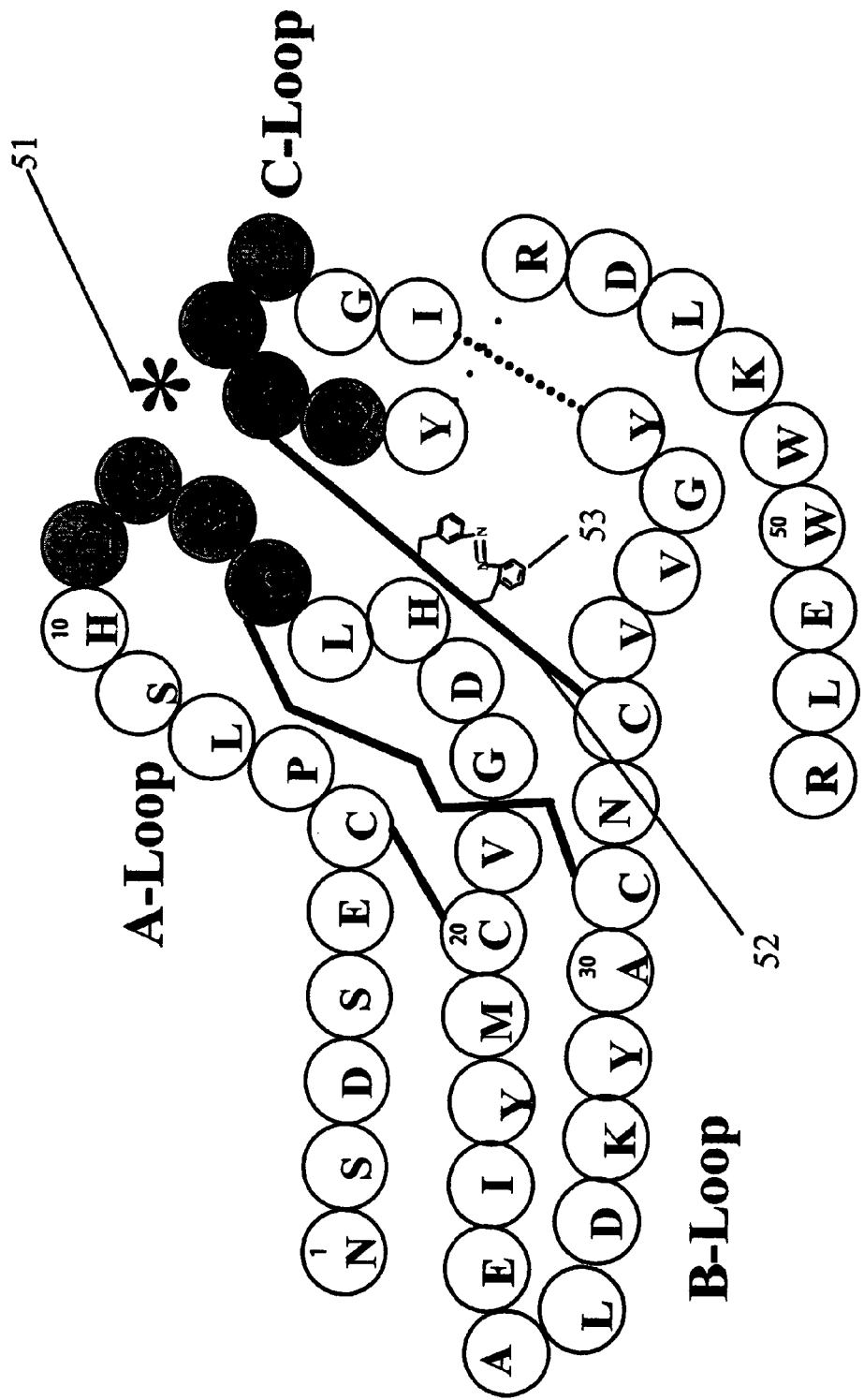
FIG. 8a shows the "active" configuration with the loops of the active site correctly folded.
Figure 8B:
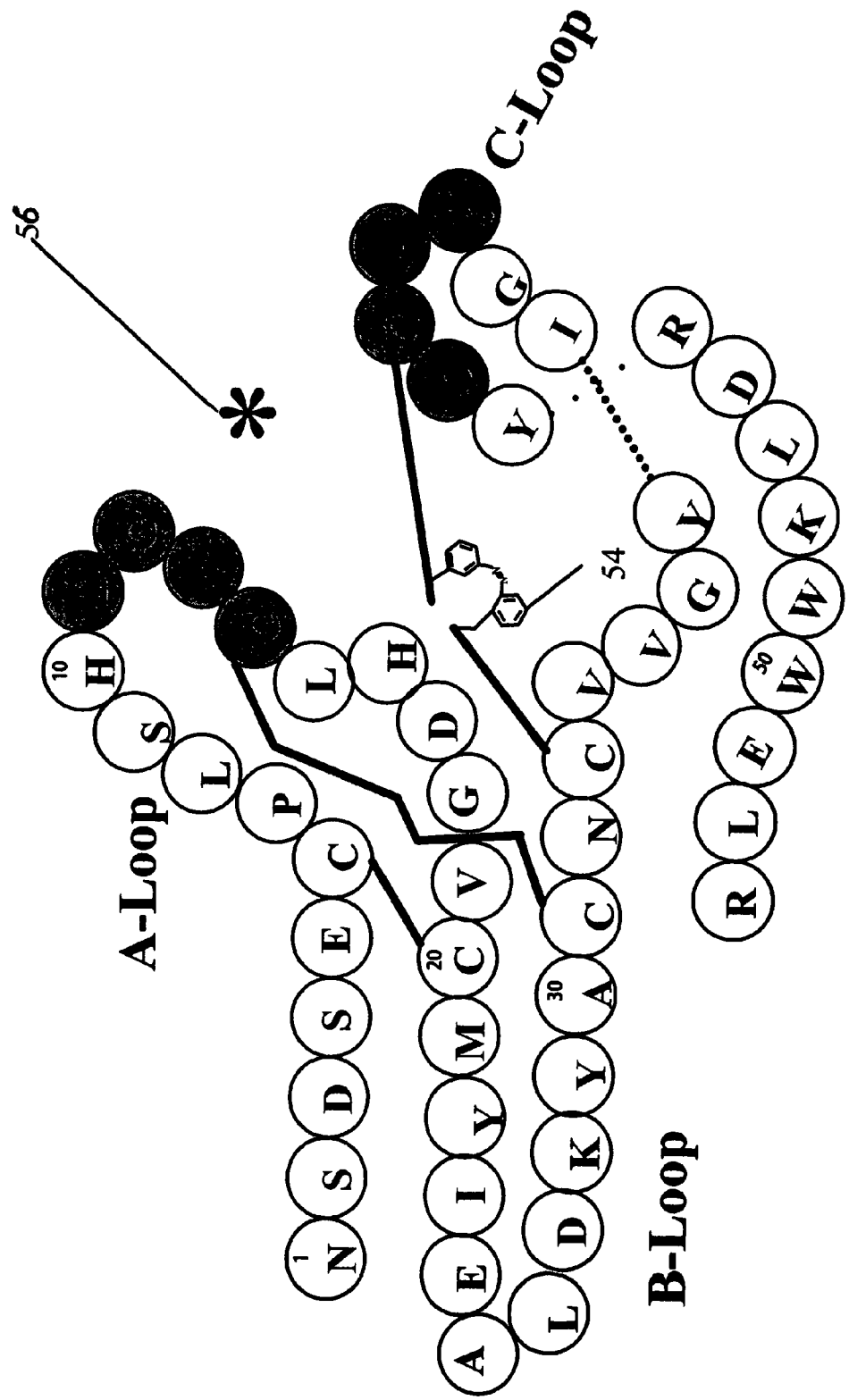
FIG. 8b illustrates how a pulse of energy to the Azobenzine moiety can render the active site non functional by separating the loops of the active site (56) too far apart to be bound by the substrate.

FIGS. 8a and 8b illustrate one embodiment of an enzyme or growth factor immobilized to the surface of a device according to this invention having an Azobenzine moiety affixed to an intraprotein linkage. In this case, the Azobenzine is in trans configuration (53) and the protein is folded correctly to expose the active site (51) which results in the correct geometry suitable for initiating the desired biological response, i.e., the "active" configuration. This geometry is disrupted when the Azobenzine converts to cis configuration (54). Note that the active site (56) is now widened and is unable to catalyze the reaction, i.e., is inactive.

Some Preferred Treating Moieties for Use in the Vascular System

Preferably, when the device is intended for use in the vascular system, the bioactive material is Sirolimus, Paclitaxel, everolimus, Plavix or another antiplatelet or antithrombotic agent, or dexamethasone, dexamethasone acetate, dexamethasone sodium phosphate, or another dexamethasone derivative or anti-inflammatory steroid.

Furthermore, a wide range of other bioactive materials can be employed, including, but not limited to, the following categories of agents: thrombolytics, vasodilators, antihypertensive agents, antimicrobials or antibiotics, antimitotics, antiproliferatives, antisecretory agents, non-steroidal anti-inflammatory drugs, immunosuppressive agents, Angiopeptin, growth factors and growth factor antagonists, Simvastatin, Progenitor cells, antitumor and/or chemotherapeutic agents, antipolymerases, antiviral agents, photodynamic therapy agents, antibody targeted therapy agents, prodrugs, sex hormones, free radical scavengers, antioxidants, nitric oxide, biologic agents, gene vectors, PCR products, DNA, RNA, antisense constructions, oncogenes, phosphorylcholine, nitrosglutathione and derivatives, angiopeptin, Latrunculin and derivatives, stem cell fragments, radiotherapeutic agents, radiopaque agents and radiolabelled agents. For example, tamoxifen citrate, Taxol® or derivatives thereof. Proscar®, Hytrin®, or Eulexin® may be applied to the tissue-exposed surface of the device for delivery to a tumor located, for example, in breast tissue or the prostate or other tissues including, but not limited to, liver, kidney, head and neck, pharynx, thyroid, pancreas, stomach, colon, colorectal, uterus, cervix, bone, bone marrow, testes, brain, neural tissue, ovary, skin, and lung.

A wide range of other bioactive materials can be affixed to the stent either directly or via linker bond including, but not limited to: heparin, covalent heparin, low molecular weight herparin formulations (e.g., Lovanox®), or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; c-myc Antisense (AVI-4126) Phosphorylcholine, a fibrinolytic agent; a vasospasm inhibitor; a calcium channel blocker, a nitrate, nitric oxide, a nitric oxide promoter or another vasodilator; Hytrin® or other antihypertensive agents; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; tamoxifen citrate, Taxol® or the derivatives thereof, or other anti-cancer chemotherapeutic agents; dexamethasone, dexamethasone sodium phosphate, dexamethasone acetate or another dexamethasone derivative, or another anti-inflammatory steroid or non-steroidal antiinflammatory agent; cyclosporin or another immunosuppressive agent; trapidal (a PDGF antagonist), angiopeptin (a growth hormone antagonist), angiogenin, a growth factor or an anti-growth factor antibody, or another growth factor antagonist; dopamine, bromocriptine mesylate, pergolide mesylate or another dopamine agonist; $^{60}$Co (5.3 year half life), $^{192}$Ir (t ½=73.8 days), $^{32}$P(t ½=14.3 days), $^{111}$In(t ½=68 hours), $^{90}$Y(t ½=64 hours), $^{99}$m Tc(t ½=6 hours) or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radio-labelled form of any of the foregoing; estrogen or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs; Proscar®, Hytrin® or other agents for treating benign prostatic hyperplasia (BHP) or a mixture of any of these; and various forms of small intestine submucosa (SIS).

FIG. 8*a* illustrates an EGF monomer linked to the surface of a device. FIG. 8*b* demonstrates use of the invention to facilitate the EGF/EGFr cascade in vivo. Note that the active moieties can be bound to the device as a "dimeric" arrangement (FIG. 8*b*). Presentation of the EGF binding domains adjacent to each other facilitates activation of the complex, since diffusion of free EGF in solution and random receptor binding on widely separated membrane bound receptors is facilitated by at least two of the four needed molecules being fixed and not subject to random molecular movement. In contrast to the prior art, the treating material can remain attached to the surface of the device during activation of the intracellular reaction. Following activation of its tyrosine kinase, the cell is released from the device and another cell is free to take its place.

As discussed above, two or more different active moieties, e.g., growth-altering, blood-thinning or thrombogenic molecules, can be combined on a single device. Presentation of their active sites can be controlled by a "circuit" arrangement as also described above. Given this controllability, temporal activation of these different moieties can be tailored to take full advantage of advances in the biology of, for example, endothelial proliferation and prevention thereof.

Example 4

Treatment of Undesirable Cells

There are instances in which cell death or protein inactivation is the desired result, rather than inhibition of cell growth or molecular formation. This invention is ideally suited for these purposes since molecules which initiate these reactions can be bound covalently to the device and switched on and off as needed. There are many mechanisms by which the body can eliminate undesired cells or proteins. For example, proteins are often phosphorylated or appended with polypeptides or cleaved in the course of cellular events either to rend them inactive or to initiate a specific intracellular cascade resulting in cell death. Other enzymatic reactions on the cell surface can lead to the activation of ligases within the cytoplasm designed to cleave specific proteins or nucleic acids. A device-bound protein kinase is ideal for the former process, while a device-bound ligase or similar molecular entity can perform the latter. Tyrosine kinase receptors are a family of receptors with a similar structure. Each tyrosine kinase receptor has a tyrosine kinse domain (which phosphorylates proteins on tyrosine residues), a hormone binding domain, and a carboxyl terminal segment with multiple tyrosines for auto-phosphorylation.

When a native hormone, or in this case, the hormone-like moiety bound to the device binds to the extracellular domain, the receptors aggregate. When the receptors aggregate, the tyrosine kinase domains phosphorylate the C terminal tyrosine residues. This phosphorylation produces binding sites for proteins with SH2 domains (e.g., GRB2). GRB2 bound to SOS, then binds to the receptor complex causing activation of SOS. SOS is a guanyl nucleotide-release protein (GNRP). When activated, SOS causes certain G proteins (e.g., Ras) to release GDP and exchange it for GTP. When ras has GTP bound to it, it becomes active and causes activation of a cellular kinase called raf-1. Raf-1 kinase then phosphorylates another cellular kinase called MEK causing the activation of MEK. Activated MEK then phosphorylates another protein kinase called MAPK causing its activation. Among the final targets of the kinase cascade are transcription factors (fos and jun are common examples). Phosphorylation of these proteins causes them to become active and bind to the DNA, causing changes in gene transcription and in some cases the subsequent death of the cell. Perhaps the most well-studied of these apoptotic kinases is "Death associated protein kinase family", or DAPK.

DAPK contains a "death domain" that can initiate a cascade of molecular events that cause a cell to commit suicide. This process, called programmed cell death or apoptosis, is programmed into all but the most primitive of cells causing the cell to shut down in an orderly manner so that its contents can be absorbed by surrounding cells without initiating an attack by the body's internal self-defense systems. This invention provides means to selectively activate DAPK such that only cells in contact with the implantable device of the invention will be affected. Thus, the invention can be "cleaned off" without affecting cells not close to the device simply by activating the DAPK by the external application of energy to the device.

One problem with long term use of DES stent placement is that the device can become covered by fibroblasts or other undesirable cells, thereby limiting the availability of elutable treating materials. This invention solves this problem by being capable of "turning on" membrane-based apoptosis enzymes and/or Na+/K+ pump poisons in the cells covering the device. In this way, only the cells actually covering the device will be affected, because only cells in direct contact with the device are activated by the bound treating moiety. This cell death signal can be applied as a short pulse, thereby "cleaning" the surface of the stent of undesirable cells. The primary treating program can then be reactivated.

Example 5

Construct for the Treatment of Cancer

Among the most commonly implicated molecules in the transformation of normal cells to cancer cells is the malfunctioning of the growth factors, e.g., epidermal growth factor (EGF). Systemic drugs, e.g., herceptin, have recently been developed to act upon the HER2/Neu receptor with results in breast cancer. By placing a device according to this invention in the primary blood supply to the tumor, it provides the active domain of the HER2/Neu receptor locally, eliminating the need for systemic chemotherapy. As the domain is reusable, it advantageously reduces exposure to the toxic drug, as well as reduces cost.

The HER2/Neu receptor is not the only cascade which can be activated by devices according to this invention. EGF and others, e.g., TGF alpha, act through a class of receptor domains using the ErbB signaling network. The ErbB signaling network is composed of the ErbB1 (or EGFR), ErbB2 (HER2/Neu), ErbB3 (HER3), and ErbB4 (HER4) tyrosine kinase receptors. Upon ligand binding, these receptors dimerize into a variety of homodimeric and heterodimeric receptor complexes whereby the intrinsic kinases become activated, which results in a cascade of second messengers and a diversity of subsequent downstream signaling similar to that discussed above. ErbB receptors play an important role in growth and differentiation of cells, whereas overexpression of both receptors and ligands has been found in several human cancers. As a consequence, the ErbB signaling network is increasingly used as a therapeutic target for the development of anti-tumor drugs, and thus is an excellent application of this invention. Although drugs are administered systemically, this invention advantageously localizes the treatment effects of these most potent mediators, to the site they are needed and thus do not elicit systemic complications.

Despite having distinct receptor binding specificity, all ErbB growth factors have an EGF-like domain as a common motif, which is defined by three disulfide bridges that generate three looped regions, designated the A-, B-, and C-loop, in addition to linear N and C termini. A single hinge residue between the fourth and fifth cysteine divides the EGF-like ligand into an N- and C-terminal half, each with a two-stranded antiparallel-sheet. This invention takes advantage in this "hinge" by opening and closing it by means of a neighboring Azobenzine group.

Modification of EGF-Like Domain Activity In Vivo

Since it is now clear that specific residues in the B-loop region of EGF are involved in binding to the first extracellular domain (domain I) of the ErbBl receptor, it is these residues in the B-loop region of EGF which can be "hidden" from domain I of the ErbB1 receptor by Azobenzine-induced conformational change. Although the native EGF molecule contains three cistiene linkages suitable for Azobenzination, the preferred linkage is the 33-42 linkage, as it can exert maximum control over the active site confirmation and is remote from the B-loop which is the portion of the EGF molecule affixed covalendy to the invention. (FIGS. 8*a* and 8*b*). In this invention, the methods of Kumita are preferred. (Kumita, J. R., Smart, O. S. and Woolley, G. A. (2000) *Proc. Nat'l Acad. Sci. USA,* 97, 3803-3808).

Other Cell Death Mediators can Also be Used with the Invention

The immune system is designed to rid the body of undesirable cells and circulating cancer cells. Horvath, et al. (U.S. Pat. No. 6,663,863) refer to the use of medicines derived from the complement domains of the immune system to inhibit cell adhesion. These authors refer to use of these compounds to inhibit recruitment and/or adhesion of cells to the site of vascular injury. The complement cascade also facilitates cell death interactions between immune cells and foreign organisms.

For example, the compliment cascade can be initiated on cells, e.g., fibroblasts, which may undesirably cover parts of the device of the invention rendering it sub optimally active. By initiating the compliment cascade on these fibroblasts, they will be eliminated by the immune cells, and the device can be made "as new" as when it was deployed. If one deploys the devices according to the invention on the dura matter overlying the site of a resected meningioma, this cascade can be initiated on the recurrent tumor, should its return pose a clinically significant problem. If an antifungal function is desired topically, a similar sheet could contain, for example, enzymes specific to fungal apoptosis.

Example 6

Treating Diseases of the Nervous System

The neurotrophins, e.g., Nerve Growth Factor (NGF), bind to two completely different cell surface receptors, the Trk tyrosine kinase receptors (TrkA, TrkB, and TrkC) and the shared p75 receptor. These different ligand-receptor interactions produce multiple different effects on their host neurons, lasting from milliseconds to days. These effects include, but are not limited to neuronal cell plasticity and survival. Furthermore, each receptor forms myriad interactions with other plasma membrane receptors. The Trk receptors, i.e., the high-affinity receptors, interact with ion channels, such as TRPC3, the TRPVl capsaicin receptor, and a voltage-sensitive sodium channel. In contrast, p75, i.e., the low-affinity receptor, associates with the leucine-rich repeat proteins Nogo receptor and LINGO, which are involved in axonal regeneration, and sortilin, a trafficking receptor that brings the precursor form of NGF (proNGF) together with p75. (Wiesmann and de Vos A M., Cell Mol Life Sci. 2001 May; 58(5-6):748-59).

The High affinity NGF receptor contains two leucine-rich motifs (LRMs) flanked by cysteine-rich clusters (see Schneider, R., and Schweiger, M. (1991) *Oncogene* 6, 1807-1811). Exposure of the LRM segments of the TrkA to neurotropin can be controlled by the addition of an Azobenzine moiety to any of the cistiene residues in the CII segment. The CI segment is less preferred, as the conformational change elicited by activation of the Azobenzine group in that location is less dramatic. Similarly, the NGF molecule itself can be affixed to the device using the 5' carboxylic acid residue and the cistiene residues flanking the beta pleated sheet, i.e., the receptor binding domain of the growth factor, can be modified with Azobenzine groups. The addition of the Azobenzine groups can be accomplished using the methods of Kumita et al, as above.

Peripheral Nerve Regeneration

Many tissues can be injured in traumatic events; however this invention also provides means to improve the healing of, perhaps, the most recalcitrant of tissues—neurons and their processes. When peripheral nerves are severed, they typically regrow along or within the sheath of supporting cells that once contained the healthy axon. Sometimes, however, this sheath is absent due to overwhelming trauma, or is unusable because it cannot be found in surgery. The growth and extension of an axon growth cone requires expression of several molecules, many of them enzymes or growth factors such as Brain Derived Growth Factor, in a precise order. Expression of molecules in this order is repeated along the sheath as the axon grows distally. This invention can provide for expression of this repetitive sequence of molecular presentation. Lengths of "axon sheath" can be formed with this device; the temporal expression of surface molecules controlled by a "circuit", as the needs of the axon require.

If a permanent denervation of an area is desired, one can manufacture the device with local Na/K pump poisons or Acetyl Choline receptor blocker activity. For example, a current use of injectable Botulinum Toxin is to produce local facial nerve denervation. Unfortunately, the injected activity wears off, necessitating repeat injection. If one implants the invention as described above, one can eliminate the need for repeat injection of compounds such as Botulinum Toxin, as the Acetyl Choline receptors are continually blocked by the device and the blockers do not wash away or get used up.

Treatment of Movement Disorders Locally

Dopamine or a dopamine agonist such as bromocriptine mesylate or pergolide mesylate is useful for the treatment of neurological disorders such as Parkinson's disease. In one embodiment, a device made in accordance with the invention could be placed as a stent in the vascular supply of the thalamic substantia nigra for this purpose, or elsewhere, localizing treatment in the basal ganglia, cortex, thalamus, brainstem, or midbrain. The device, if designed as a stent or indwelling catheter, is easily tracked to these areas using routine interventional neuroradiological techniques. Pro-drugs can thus be converted to active drugs as described herein, thereby maximizing their localization and effects, while minimizing side effects.

Example 7

Treatment of Systemic Conditions Such as Diabetes

The use of devices according to the invention is not limited to treating a surface of blood vessels. For example, the methods and devices of the invention are also applicable to the conversion of pro insulin to insulin, the understanding of which has revolutionized the treatment of diabetes. Current therapies taking advantage of this system utilize drug therapy to provide insulin in the correct dosages to diabetics. One current problem in administering the correct dosage of insulin is that guesses must be made as to the expected level of blood sugar after meals. If too much insulin is administered, the patient gets hypoglycemic. If too little insulin is administered, blood sugar remains too high.

Figure 9A:
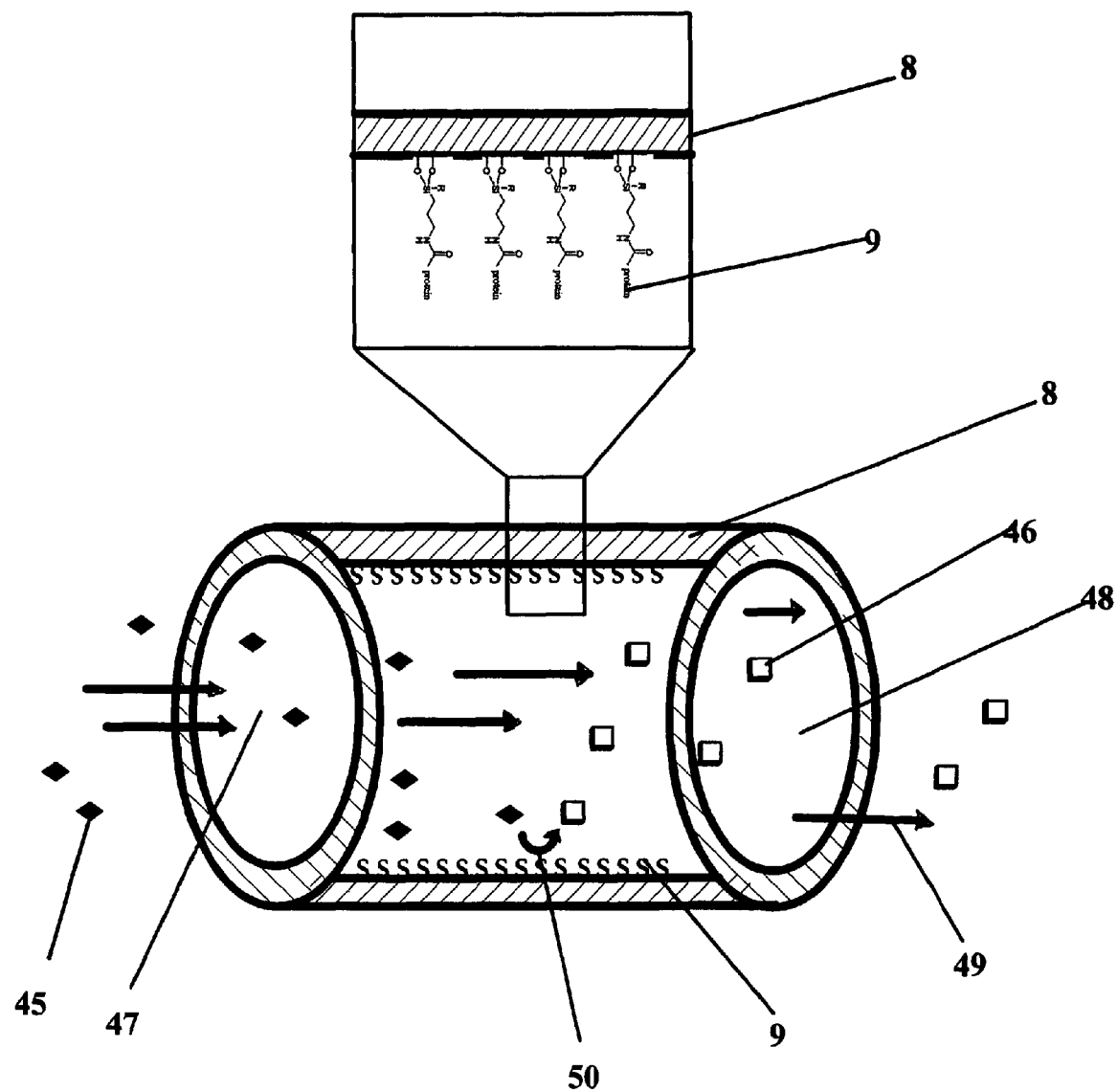
FIGS. 9a-c illustrate embodiments in which devices according to preferred embodiments of the invention can be used in vitro.

FIG. 9a demonstrates how the device can be used while implanting the invention in a artery to deliver drugs to target tissues downstream. Note that the device (8) is converting a pro drug (45), in this case, pro insulin to an active drug (46) in the blood. Flow is represented by 49 The blood prior to entering the device (47) contains the prodrug (45) in solution. The reaction catalyzing the conversion from pro drug (45) to active drug (46) is shown (50). If the device is made as a transistor as depicted in FIGS. 7a-d, feedback from a photocell affixed to a glucosimeter can modulate the conversion process to precisely regulate blood glucose on a real time basis. The rate or character of stimulation of the device, by a photocell or external energy source could be regulated by attachment to the cell of a feedback loop from a blood monitoring device.

Figure 9B:
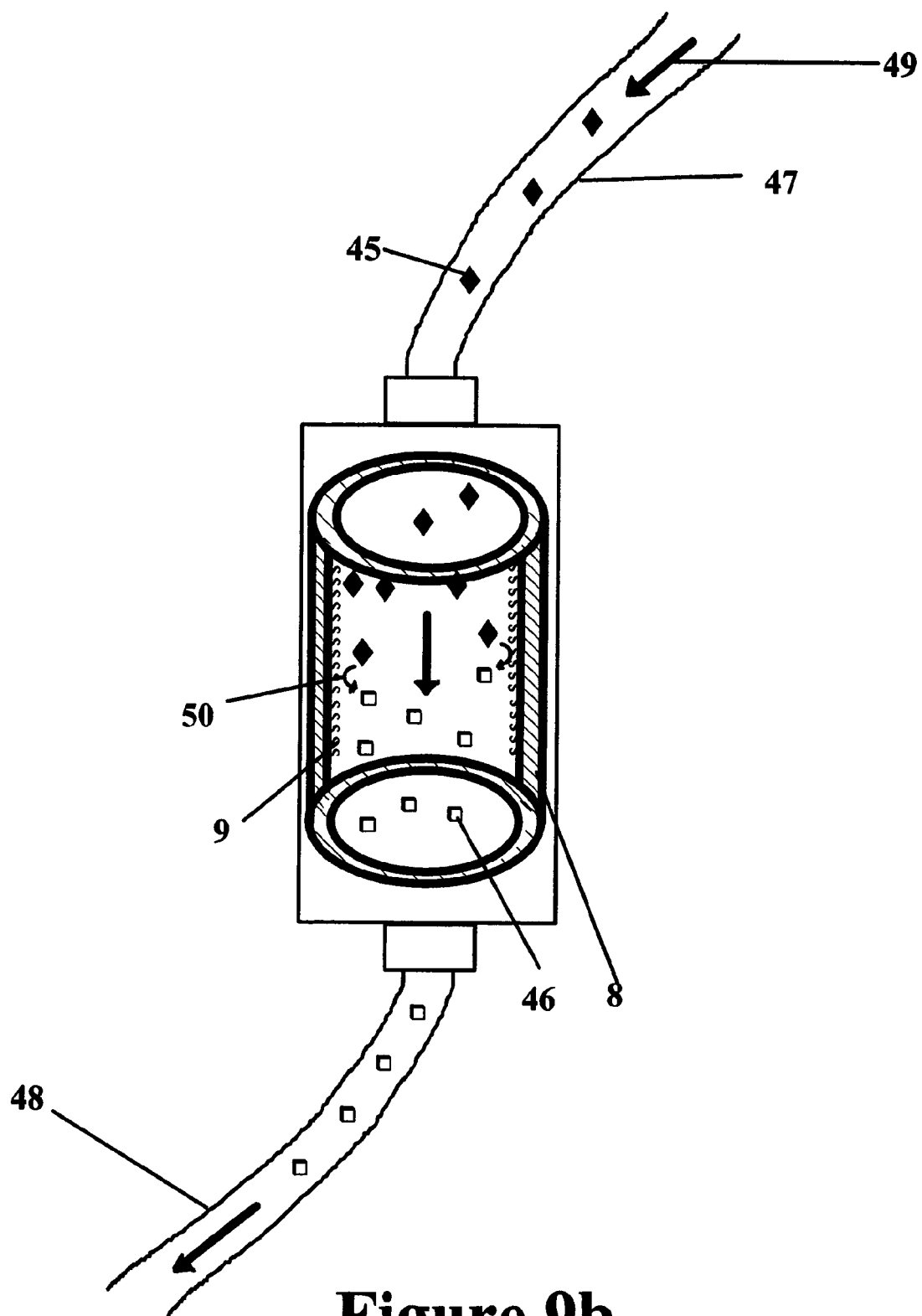

FIG. 9b shows a device according to the invention used in IV tubing.

Example 8

Local Activation of Systemic Drugs

The methods and devices of this invention can be used to present catalysts which form any number of active drugs from pro-drugs in solution, thereby eliminating the need for continued enteric administration of the active compound with its resultant systemic side effects. The monitoring system need not be directly wired to the device, rather a monitoring device adherent to the dermis could be used to transmit energy to the implanted device using, for example, skin transillumination. This dermal monitoring device could then be replaced periodically, much like is currently done with nicotine or opioid patches.

Parenterally or enterically administered pro-drugs can be converted to active drugs at the site of need, if specific enzymatic activity for their conversion is present on the device. For example, if one wished to treat hepatic metastatic lesions preferentially, one should place the device as a stent inside the hepatic artery as illustrated in FIG. 9a. In this embodiment, one could administer a pro-chemotherapeutic agent systemically, and the device would activate it when the blood in the hepatic artery flowed past. In this fashion, the liver would receive the bulk of the active chemotherapy agent, and systemic exposure would be substantially less. Another such application is the device-based stimulation of transplanted endocrine cells, such as thyroid or pancreatic islet cells, and their controlled elution of hormones into the bloodstream. FIG. 9b illustrates how a device according to the invention can be used to treat fluids ex corpora as the fluid passes through tubing.

Example 9

Treatment of Cells or Other Tissues In Vitro

Treatment of nerve cells typically requires in vivo application; however, cells (37) which are not so finicky can be grown and/or modified in vitro, if grown on a surface formed by this invention (8). Examples of these applications include growth of skin or corneal cells, stem or other progenitor cells, or endothelial cells of the GI system. Endocrine cells, such as thyroid or pancreatic islet cells, or protein secreting cells, such as "B" cells of the immune system, can also be controlled by the device in vitro, and their products can then be used in the medical therapy. In vivo applications of this type include enzymatic stimulation of the cochlea in conductive hearing loss, or stimulation or "temporary deadening" of the taste buds during ingestion of a particularly noxious drug. Nutritive media (38, 39), and flow in the petri dish (40) are shown.

Figure 9C:
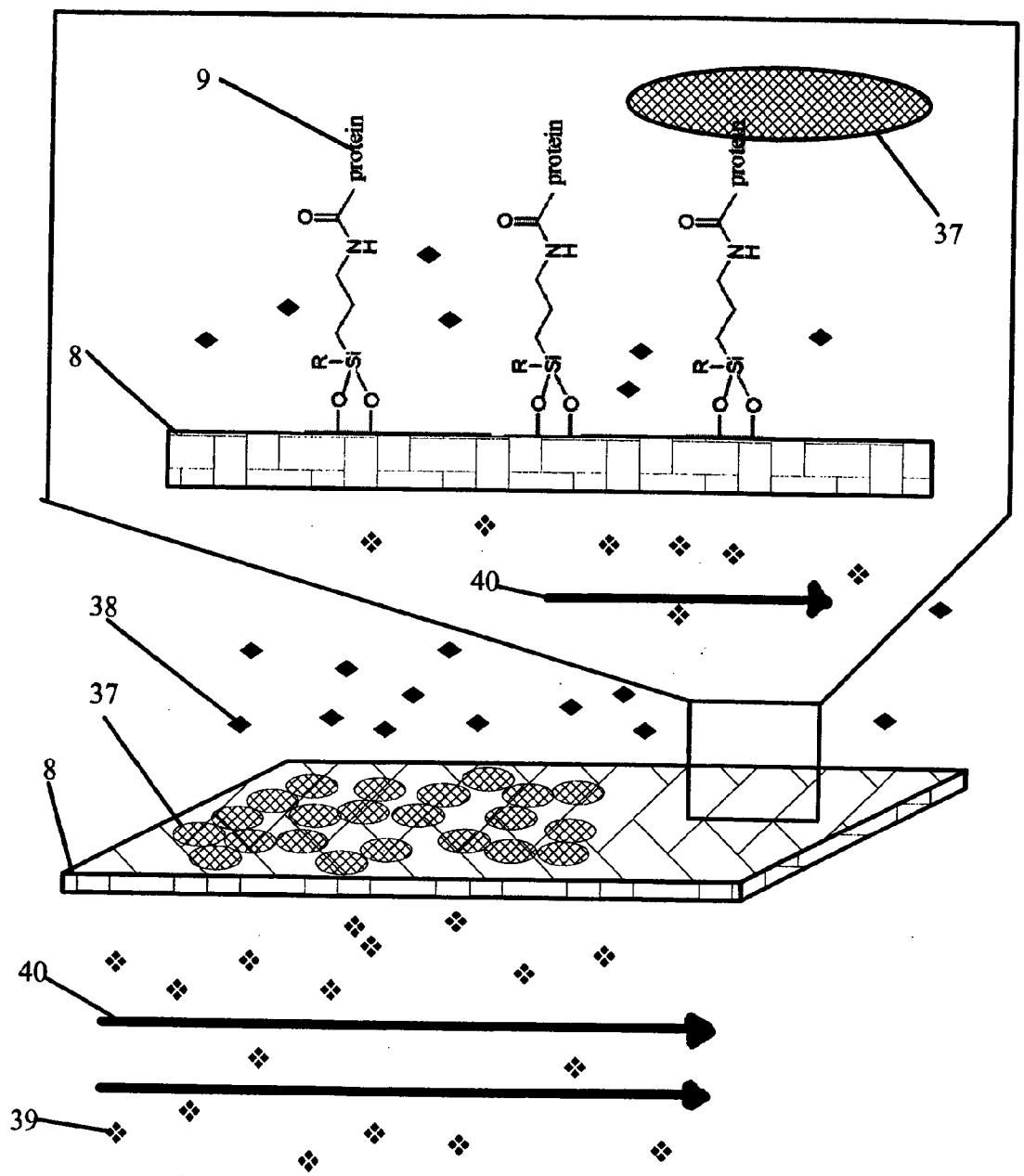

FIG. 9c demonstrates how another embodiment of the invention can be used to treat cells and/or tissues in vitro, or, in the case of an islet cell transplant or parathyroid transplant, in vivo. Cells (37) are grown on the surface of the device (8). The enzymatic active sites (9) can be modulated via electric current applied to the device, or as a continuous (always on) form. The tissues, e.g., cells, can be stimulated at predetermined intervals according to biological need. As above, feedback to the device can be provided by a monitoring system, e.g., glucosometer or Calcium ion monitor, and relayed through the photocell. The device can also be made capable of restraining some molecular entities through size, electric charge, or hydrophobic interactions. The illustration in FIG. 9c also demonstrates how the device can treat cells and/or molecules on a mucosal surface. If the device (8) is composed of a clear compound, a contact lens or sheet of cornea can have enzymatic moieties affixed for presentation to the fluids of the eye. Similarly, if manufactured on a plastic film, the device can be used to treat lesions of the skin so that fibroblasts and other cells are activated—thereby increasing the rate of healing or decreasing scar formation.

Example 10

Manufacture and Use of a Stent Having DAPK Surface Modification for Treating Cancer In this example, the device to be used is a stainless steel biliary stent coated with the active domain of DAPK so that malignant cells growing adjacent to the stent are induced to die according to the DAPK-induced apoptotic cascade.

The preferred but by no means exclusive steps of this process are outlined below:
Preparation of the Stent:
A stent manufactured with stainless steel is to be provided. The metallic surface of the stent can be anodized using a strong acid in the usual fashion. The resultant stent will have a reactive oxide on its surface as was described above. One can then either coat the stent with a commercially available silane preparation prior to reacting the DAPK moiety (Corning Life Sciences, Acton, Mass.), or react the oxidized metallic surface with propyl amino silane. Suitable techniques, in addition to being described above, are known in the art and have been recently reviewed by Johnston, et al, Electroanal., 7, 520-526 (1995). An additional recent review of the suitable techniques is "Adsorption of Polyamides and Polyamide-Silane Mixtures at Glass Surfaces, J. R. Shallenberger, E. E. Metwalli and C. G. Pantano, Surface and Interface Analysis, 35, 667 (2003). See also the Corning Life Sciences technical bulletin for their amino-proprio-silane (GAPS) product line.
Isolation of the Catalytic Domain Prior to Affixation
The DAPK catalytic domain can be produced, as was described by Velentza et al, (J. Biol. Chem., Vol. 276, Issue 42, 38956-38965, Oct. 19, 2001) by polymerase chain reaction-assisted subcloning from DAPK cDNA, using the primers 5'-GGG GGG GGT CTC AGC GCT CTT GAT CCA GGG ATG CTG CAA-3' (SEQ ID NO: 2) and 5'-GGG GGG GGT CTC AGC GCT ACT AAG TGC CTG TTG TGT ATC-3' (SEQ ID NO: 3), which contains flanking BsaI sites and amplified the portion of the cDNA from nucleotides 337-1191 (GenBank™ accession number NM_004938). Briefly, the region of the DAPK cDNA that encodes amino acids 1-274, corresponding to the similar catalytic region produced from myosin light chain kinase (MLCK), can be subcloned into the pASK-IBA3 (Sigma) expression vector at the BsaI sites. Protein can be produced and purified from *Escherichia coli* with the additional use of the streptavidin tag following the manufacturer's recommendations. The protein can be homogeneous by SDS-PAGE and give the expected molecular weight.

DAPK can be enriched from bovine brain extracts using a modification of the first few steps of myosin light chain kinase (MLCK) purification, with all purification steps carried out at 4° C. Briefly, bovine brain can be homogenized in 2 volumes of buffer A (20 mM Tris-HCl, pH 7.3, 1 mM EDTA, 1 mM dithiothreitol, 1 mg/liter pepstatin and leupeptin, 40 mM 1-chloro-3-tosylamido-7-amino-2-heptanone) in a Waring blender at low speed, centrifuged at 10,000×g for 30 min in a Sorvall SLA-3000 rotor, and the supernatant subjected to a 55% saturated ammonium sulfate precipitation. The 55% ammonium sulfate pellet can be resuspended in 1 volume of buffer B (20 mM Tris, pH 8.0, 1 mM EDTA, and 1 mM dithiothreitol), and its conductivity can be adjusted to that of buffer B. The redissolved fraction can be adsorbed to a DEAE-cellulose column equilibrated with buffer B, and DAPK eluted with buffer B containing 0.2 M NaCl.
Peptide Synthesis
Peptide synthesis can be done by solid phase synthesis, using a parallel synthesis of each peptide, except that the guanyl group of Arg can be protected with 2,2,4,6,7-pentamethyldihydrobenzofuran-5-sulfonyl, and 30 mg of Rink-amide resin (0.8 mmol of nitrogen/g) from Advanced ChemTech (Louisville, Ky.) can be used. Peptides can be cleaved from the resin by treatment for 3 h using a mixture of trifluoroacetic acid/anisole/dithioethanol (90:5:5 v/v/v) at room temperature. Peptides then can be precipitated with ethyl ether, and can be extracted with 5% (v/v) acetic acid, lyophilized, and then purified by reverse phase-high pressure liquid chromatography on a preparative Chromosorb (Rainin Instruments, Woburn, Mass.) C18 column using gradients of 0.1% (v/v) trifluoroacetic acid in water and 60% aqueous acetonitrile containing 0.08% trifluoroacetic acid. Purified peptides should then be characterized by matrix-assisted laser-desorption mass spectrometry (MALDI-TOF MS) using a Perspectives (Foster City, Calif.) VoyagerDE-Pro system and by amino acid composition analysis of acid hydrolysates on a Waters (Bedford, Mass.) Alliance 2690 separations system equipped with a Waters 996 photodiode array.
In Vitro Determination of Activity on the Stent Prior to Implantation
To ensure that the exposed active site is unharmed and available to the exposed tissues, western blot analyses can be done with a site-directed polyclonal rabbit antisera (number 7315) made against the synthetic peptide KPKDTQQALSRK (SEQ ID NO: 4) using a standard protocol for antibody production. This amino acid sequence corresponds to a region of the DAPK ORF that encodes the DAPK catalytic domain.

Peptide substrate phosphorylation by DAPK can be approximately linear under the conditions used, and less than 10% of the peptide can be consumed in each reaction. Kinetic data can be analyzed by double-reciprocal (Lineweaver- Burk) plots using Prism version 2.0 (GraphPad Software Inc.). Autophosphorylation of endogenous DAPK can be examined in vitro as is done routinely for calmodulin-dependent protein kinase II. Briefly, enriched fractions from the DEAE-cellulose chromatography purification step of endogenous DAPK from bovine brain, or commercially available calmodulin-dependent protein kinase II as a control, can be incubated for 10 min at 25° C. in the presence of [γ-$^{32}$P]ATP. The reaction can be terminated by addition of SDS-containing sample buffer, and samples subjected to SDS-PAGE. $^{32}$P-Labeled proteins can be visualized by STORM PhosphorImager (Molecular Dynamics) after 1 and 14 h of exposure.

Placement of the Stent In Vivo

A patient with a malignant biliary stricture of the common bile duct is selected for treatment. The patient is brought to the endoscopic suite, and sedated. Using endoscopic guidance, the common bile duct is cannulated. A 0.035 guide wire is placed across the stricture. Over the wire, the stent is advanced using fluoroscopic guidance. The stent is deployed across the stricture by removing the protective sheath. Once deployed, the stent expands to touch the tumor cells. The DAPK moiety affixed to the invention now can elicit its characteristic "cell death" cascade. The affixed DAPK catalytic domain is not used up, rather is available to multiple tumor cells during its lifetime.

Modification of Biological Activity In Vivo

The DAPK moiety has several amino acids proximal to the catalytic domain which are at least 5 Angstroms removed. Particularly suitable for substitution with the photoisomer phenylazo-1,2,3,4-tetrahydro-3 isoquinolinecarboxylic acid (PATIC) are the glutamic acid residues at positions 99 and 181. These residues are adjacent to, but not within, the catalytic domain of the molecule. These substitutions can be easily accomplished during the synthesis of the peptide following PCR and subcloning. One preferred method of PATIC use has been recently outlined by Zhang, et al, J. Peptide Res. (1999) 53:560-568. When a PATIC molecule is affixed between the catalytic domain and the stent, the PATIC will change conformation in response to externally-applied energy. The photoisomer can be stimulated from light emitted from the fiber optic component of the endoscope. Thus, the DAPK domain can be "switched on" or "off" depending on the energy emitted from the tip of the endoscope by the operator.

Accordingly, this invention can be used to treat any number of conditions, both in vivo and in vitro. Depending on the compounds presented and the temporal sequence of their activation, this invention provides the user with a method of controlling local cellular physiology by the modifications of the surface of a medical device as shown above. This device also provides a platform by which a molecular switch can be turned on and off after device deployment.

The above description and examples are only illustrative of embodiments which achieve the objects, features, and advantages of the present invention, and it is not intended that the present invention be limited thereto. Any modifications of the present invention which come within the spirit and scope of the following claims is considered part of the present invention.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

The invention claimed is:

1. An implantable medical device, comprising:
a body having a surface adapted to be placed adjacent to a biological tissue or fluid in vivo;
at least one moiety attached to the surface, wherein the moiety is capable of catalyzing a first reaction upon contacting a first substrate in the biological tissue or fluid; and
wherein the at least one moiety remains attached to the surface after the first reaction and is capable of catalyzing at least a second reaction upon contacting a second substrate.

2. A device according to claim 1, further comprising at least a second moiety attached to the surface.

3. A device according to claim 2, wherein each of the first and second moieties is capable of catalyzing a different reaction.

4. A device according to claim 1, wherein the moiety is a ligand capable of binding to a cell surface molecule.

5. A device according to claim 1, wherein the moiety is attached to the surface by a non-hydrolyzable bond.

6. A device according to claim 1, wherein the moiety is attached to the surface by a covalent bond.

7. A device according to claim 6, wherein the bond is a metaloxysilane.

8. A device according to claim 1, wherein the moiety comprises a protein.

9. A device according to claim 1, wherein the moiety comprises an aptamer.

10. A device according to claim 1, wherein the moiety comprises an enzyme.

11. A device according to claim 1, wherein the moiety comprises a growth factor.

12. A device according to claim 11, wherein the growth factor is epidermal growth factor.

13. A device according to claim 1, wherein the moiety comprises a hormone.

14. A device according to claim 1, wherein the moiety comprises a carbamide activated protein.

15. A device according to claim 1, wherein the moiety comprises a diopterine.

16. A device according to claim 15, wherein the diopterine is selected from the group consisting of FAD, FMN, and NADP.

17. A device according to claim 1, wherein the moiety comprises a redox compound.

18. A device according to claim 1, wherein the moiety comprises a nucleic acid.

19. A device according to claim 18, wherein the nucleic acid comprises a ribozyme.

20. A device according to claim 18, wherein the nucleic acid comprises an siRNA.

21. A device according to claim 1, wherein the moiety is capable of structural modification by application of energy to the device.

22. A device according to claim 1, wherein the moiety is photoisomerizable.

23. A device according to claim 22, wherein the moiety is convertible between cis to trans configuration upon exposure to a laser pulse.

24. A device according to claim 22, wherein the moiety is an azobenzine photoisomer.

25. A device according to claim 1, wherein the body is flexible.

26. A device according to claim 1, wherein the body comprises a flexible sheet.

27. A device according to claim 26, wherein the sheet has a plurality of pores.

28. A device according to claim 1, wherein the body comprises a polymeric material.

29. A device according to claim 28, wherein the polymeric material is selected from the group consisting of cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, and polytetrafluoroethylene.

30. A device according to claim 1, wherein the body comprises a metallic material.

31. A device according to claim 30, wherein the metallic material is selected from the group consisting of platinum, gold, stainless steel, tantalum, titanium, nitinol, iconel, iridium, silver, and tungsten.

32. A device according to claim 1, wherein the implantable device is a stent.

33. A device according to claim 32, wherein the stent is a vascular stent.

34. A device according to claim 2, wherein the device comprises means for converting at least one of the first and second moieties between active and inactive states.

35. A device according to claim 34, further comprising a feed back loop for activating or deactivating at least one of the first and second moieties in response to a monitored feature.

36. A device according to claim 2, wherein at least one of the first and second moieties is capable of being activated or deactivated in response to an external stimulus.

37. A device according to claim 36, wherein the external stimulus is selected from the group consisting of light, a chemical compound, a magnetic field, and an electrical signal.

38. A device according to claim 1, wherein the substrate comprises a protein.

39. A device according to claim 1, wherein the substrate comprises a cell surface protein.

40. A device according to claim 1, wherein the substrate comprises a cell surface receptor.

41. A device according to claim 1, wherein the substrate comprises a drug.

42. A device according to claim 1, wherein the substrate comprises a prodrug.

43. A device according to claim 1, wherein the substrate comprises a growth factor receptor.

44. A device according to claim 43, wherein the growth factor receptor is epidermal growth factor receptor.

45. A device according to claim 1, wherein the substrate comprises a hormone.

46. A device according to claim 1, wherein the substrate comprises a nucleic acid.

47. A device according to claim 46, wherein the nucleic acid comprises a ribozyme.

48. A device according to claim 46, wherein the nucleic acid comprises an siRNA.

49. A device according to claim 1, wherein at least of the first reaction and the second reaction comprises a reaction regulated by activation of a cell membrane receptor.

50. A device according to claim 1, wherein at least of the first reaction and the second reaction comprises activation of a cytoplasmic kinase domain.

51. A device according to claim 1, wherein at least of the first reaction and the second reaction comprises conversion of a prodrug into a pharmaceutically active agent.

52. A method of making an implantable medical device, comprising:
   providing a body having a surface adapted for placement adjacent to a biological tissue or fluid in vivo; and
   attaching at least one chemical moiety to the surface, wherein the moiety is capable of catalyzing a first reaction upon contacting a first substrate in the biological tissue or fluid and remaining attached to the surface after the first reaction, and is capable of catalyzing at least a second reaction upon contact with a second substrate.

53. A method for catalyzing a physiological reaction in vivo, comprising:
   providing an implantable device having a body and a surface thereon adapted to be placed adjacent to a biological tissue or fluid in vivo, and having at least one chemical moiety attached to the surface, wherein the moiety is capable of catalyzing a first reaction upon contacting a first substrate in the biological tissue or fluid and remaining attached to the surface after the first reaction, and is capable of catalyzing a second reaction upon contact with a second substrate; and
   implanting the device into an animal or human such that the moiety contacts a biologically activatable substrate to catalyze a physiological reaction.

* * * * *